United States Patent
Pertel et al.

(10) Patent No.: US 11,732,041 B2
(45) Date of Patent: Aug. 22, 2023

(54) ANTIBODIES AGAINST 4G7-DERIVED CHIMERIC ANTIGEN RECEPTORS

(71) Applicant: ALLOGENE THERAPEUTICS, INC., South San Francisco, CA (US)

(72) Inventors: Thomas Charles Pertel, San Mateo, CA (US); Barbra Johnson Sasu, San Francisco, CA (US); Tao Sai, Foster City, CA (US)

(73) Assignee: ALLOGENE THERAPEUTICS, INC., South San Francisco, CA (US)

( * ) Notice: Subject to any disclaimer, the term of this patent is extended or adjusted under 35 U.S.C. 154(b) by 622 days.

(21) Appl. No.: 16/851,691

(22) Filed: Apr. 17, 2020

(65) Prior Publication Data

US 2020/0331998 A1    Oct. 22, 2020

Related U.S. Application Data

(60) Provisional application No. 62/836,242, filed on Apr. 19, 2019.

(51) Int. Cl.
| | |
|---|---|
| *C07K 16/28* | (2006.01) |
| *C07K 16/42* | (2006.01) |
| *A61K 35/17* | (2015.01) |

(52) U.S. Cl.
CPC .......... *C07K 16/2803* (2013.01); *A61K 35/17* (2013.01); *C07K 16/4241* (2013.01); *C07K 2317/565* (2013.01); *C07K 2317/622* (2013.01); *C07K 2317/92* (2013.01)

(58) Field of Classification Search
CPC .......................... C07K 16/208; C07K 16/4241
See application file for complete search history.

(56) References Cited

U.S. PATENT DOCUMENTS 10,047,121 B2 * 8/2018 Barghorn ................ A61P 25/00
11,072,652 B2 * 7/2021 Vousden .............. G01N 33/564

FOREIGN PATENT DOCUMENTS

| WO | WO2014184143 A1 | 11/2014 |
| WO | WO2018023100 A2 | 1/2018 |
| WO | WO2019027850 A1 | 2/2020 |

OTHER PUBLICATIONS

Almagro et al., Front. Immunol., 8:1751, doi: 10.3389/fimmu.2017.01751 (Year: 2018).*
EPO, "International Search Report and Written Opition", mailed for PCT/US2020/028729 dated Jul. 29, 2020.
Jena, Bipulendu, et al., "Chimeric Antigen Receptor (CAR)-Specific Monoclonal Antibody to Detect CD19-Specific T Cells in Clinical Trials", PLoS ONE 8(3): e57838; https://doi.org/10.1371/journal.pone.0057838, (2013).
Pan, Ying, et al., "Anti-idiotypic antibodies: biological function and structural studies", FASEB J, vol. 9, pp. 43-49, (1995).
Smith-Bell, Sam, "Generation of FMC63 scFv specific anti-idiotype antibodies for quality control of anti-CD19 CAR T cell trials", Report submitted to Univ. Otago, Dunedin, New Zealand, (Jan. 1, 2019).

* cited by examiner

*Primary Examiner* — Jessica H Roark
(74) *Attorney, Agent, or Firm* — Allogene Therapeutics, Inc.

(57) ABSTRACT

Provided herein are isolated antibodies that specifically bind anti-CD19 chimeric antigen receptors (CARs) derived from a 4G7 scFv. Also provided are methods of making and using these isolated antibodies.

29 Claims, 14 Drawing Sheets

Specification includes a Sequence Listing.

ANTIBODIES AGAINST 4G7-DERIVED CHIMERIC ANTIGEN RECEPTORS

CROSS REFERENCE

The present application claims the benefit of priority to U.S. Provisional Application No. 62/836,242, filed on Apr. 19, 2019, the content of which is hereby incorporated by reference in its entirety.

REFERENCE TO SEQUENCE LISTING

This application is being filed electronically via EFS-Web and includes an electronically submitted sequence listing in .txt format. The .txt file contains a sequence listing entitled "AT-020_02US_SL_ST25" created on Apr. 16, 2020, and having a size of 40,343 bytes. The sequence listing contained in this .txt file is part of the specification and is incorporated herein by reference in its entirety.

TECHNICAL FIELD

The instant disclosure relates to antigen binding molecules, such as antibodies, which specifically bind to the scFv portion of chimeric antigen receptors (CARs) derived from 4G7 that bind to human CD19, polynucleotides encoding the same, and methods of manufacturing and treating a cancer in a patient using the same.

BACKGROUND

Anti-idiotypic antibodies are a subset of antibodies raised against immunizing antibodies. These anti-idiotypic antibodies demonstrated specific binding against the idiotopes (unique antigenic determinants on the surface of the antibodies) of the immunizing antibodies. Anti-idiotypic antibodies can be generally classified into three distinct groups: (1) antibodies that recognize idiotopes distinct from the antigen-binding site (ABS) on immunizing antibodies; (2) antibodies that recognize epitopes within the ABS and mimic the structure of the nominal antigen; and (3) antibodies that recognize epitopes within the ABS without the structural resemblance of the nominal antigen (see, e.g., Pan et al., (1995) *FASEB J* 9:43-49).

Prior methods to detect CAR expression (e.g., an anti-murine Fab antibody, soluble human CD19-Fc fusion protein) can lack specificity, have batch-to-batch variability, produce low intensity signals in analytical methods (e.g., flow cytometry), or be difficult to make in sufficient quantities, which can underestimate the true number CAR expressing cells.

Thus, there is a need for robust reagents to accurately detect CAR expression on engineered T cells or in in vitro assays. Provided herein are methods and compositions addressing this and other needs.

SUMMARY

The present disclosure provides robust reagents with specific high affinity binding to detect anti-CD19 CARs comprising an scFv portion derived from antibody clone 4G7 (e.g., UCART19, ALLO-501 and ALLO-501A). Antibodies described herein can be used in a method to detect anti-CD19 CAR expression in the context of non-clinical research studies, manufacturing of immune cells comprising a 4G7 derived scFv (e.g., UCART19, ALLO-501 and ALLO-501A), as a clinical flow-based pharmacokinetic reagent and in clinical immunogenicity studies.

In one aspect, the present disclosure provides an isolated antibody that specifically binds a molecule comprising an anti-CD19 scFv derived from 4G7, and in one embodiment the antibody is humanized. In some embodiments, the anti-CD19 scFv derived from 4G7 comprises an amino acid sequence that is at least 80%, at least 90%, at least 95%, at least 97%, at least 99%, or 100% sequence identity with the amino acid sequence of SEQ ID NO:36. In some embodiments, the isolated antibody does not bind to a framework region of 4G7. In some embodiments, the isolated antibody binds to an anti-CD19 scFv derived from 4G7 with a KD of no more than 100 pM, no more than 90 pM, no more than 80 pM, no more than 70 pM, no more than 60 pM, no more than 50 pM, no more than 40 pM, no more than 30 pM, or no more than 20 pM, as determined by a Biacore assay at 25° C. In various embodiments an antigen binding molecule is selected from the group consisting of an antibody, an scFv, a Fab, a Fab', a Fv, a F(ab')$_2$, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG3 antibody having at least one mutation in the hinge region, an IgG4 antibody, an IgG4 antibody having at least one mutation in the hinge region, an antibody comprising at least one non-naturally occurring amino acid, and any combination thereof.

In further embodiments an isolated antibody comprises a heavy chain (HC), and in specific embodiments the HC comprises a heavy chain variable region (VH) sequence selected from the group consisting of SEQ ID NOs: 1-3. In further specific embodiments of an antibody provided herein comprises a heavy chain CDR1 selected from the group consisting of SEQ ID NOs: 15, 21, 24, and 29. In additional specific embodiments of an antibody provided herein comprises a heavy chain CDR2 selected from the group consisting of SEQ ID NOs: 16, 22, 25, 30, 31, and 33. In yet other embodiments of an antibody provided herein comprises a heavy chain CDR3 selected from the group consisting of SEQ ID NOs: 17, 23, and 26. In still further embodiments a heavy chain of an antibody provided herein comprises a heavy chain CDR1, a heavy chain CDR2, and a heavy chain CDR3, each CDR comprising an amino acid sequence shown in Table 1c.

In some embodiments an antibody comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule provided herein.

In some embodiments an isolated antibody provided herein comprises alight chain (LC), and in various embodiments a LC comprises a light chain variable region (VL) sequence selected from the group consisting of SEQ ID NOs: 7-10. In some embodiments a light chain variable region (VL) of an antibody provided herein comprises one or more of (a) a CDR1, (b) a CDR2, and (c) a CDR3. In further specific embodiments a light chain CDR1 of an antibody provided herein can be selected from the group consisting of SEQ ID NOs:18 and 27. In other embodiments a light chain CDR2 of an antibody provided herein can comprise SEQ ID NO: 19. In still further embodiments a light chain CDR3 of an antibody provided herein can be selected from the group consisting of SEQ ID NOs: 20, 28, and 32. In still further embodiment a light chain of an antibody provided herein comprises a light chain CDR1, a light chain CDR2 and a light chain CDR3, each CDR comprising an amino acid sequence in Table 1d.

In some embodiments a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule provided herein.

In an embodiment an antibody provided herein comprises (a) a VH comprising the amino acid sequence of SEQ ID NO:1; and (b) a VL comprising the amino acid sequence of SEQ ID NO: 7. In another embodiment an antibody provided herein comprises (a) a VH CDR1 comprising the amino acid sequence of SEQ ID NO:15; (b) a VH CDR2 comprising the amino acid sequence of SEQ ID NO: 16; (c) a VH CDR3 comprising the amino acid sequence of SEQ ID NO: 17; (d) a VL CDR1 comprising the amino acid sequence of SEQ ID NO: 18; (e) a VL CDR2 comprising the amino acid sequence of SEQ ID NO: 19; and (f) a VL CDR3 comprising the amino acid sequence of SEQ ID NO: 20. In a further embodiment an antibody provided herein comprises (a) a VH comprising the amino acid sequence of SEQ ID NO: 2; and (b) a VL comprising the amino acid sequence of SEQ ID NO: 8. In a further embodiment an antibody provided herein comprises (a) a VH CDR1 comprising the amino acid sequence of SEQ ID NO: 24; (b) a VH CDR2 comprising the amino acid sequence of SEQ ID NO: 25; (c) a VH CDR3 comprising the amino acid sequence of SEQ ID NO: 26; (d) a VL CDR1 comprising the amino acid sequence of SEQ ID NO: 27; (e) a VL CDR2 comprising the amino acid sequence of SEQ ID NO: 19; and (f) a VL CDR3 comprising the amino acid sequence of SEQ ID NO: 28.

In an embodiment an antibody provided herein comprises (a) a VH comprising the amino acid sequence of SEQ ID NO: 3; and (b) a VL comprising the amino acid sequence of SEQ ID NO: 9. In a specific embodiment an antibody provided herein comprises (a) a VH CDR1 comprising the amino acid sequence of SEQ ID NO: 24; (b) a VH CDR2 comprising the amino acid sequence of SEQ ID NO: 31; (c) a VH CDR3 comprising the amino acid sequence of SEQ ID NO: 26; (d) a VL CDR1 comprising the amino acid sequence of SEQ ID NO: 27; (e) a VL CDR2 comprising the amino acid sequence of SEQ ID NO: 19; and (f) a VL CDR3 comprising the amino acid sequence of SEQ ID NO: 32. In another embodiment an antibody provided herein comprises (a) a VH comprising the amino acid sequence of SEQ ID NO: 1; and (b) a VL comprising the amino acid sequence of SEQ ID NO: 10. In another embodiment an antibody provided herein comprises (a) a VH CDR1 comprising the amino acid sequence of SEQ ID NO: 15; (b) a VH CDR2 comprising the amino acid sequence of SEQ ID NO: 16; (c) a VH CDR3 comprising the amino acid sequence of SEQ ID NO: 17; (d) a VL CDR1 comprising the amino acid sequence of SEQ ID NO: 18; (e) a VL CDR2 comprising the amino acid sequence of SEQ ID NO: 19; and (f) a VL CDR3 comprising the amino acid sequence of SEQ ID NO: 20.

In some embodiments, the isolated antibody comprises a heavy chain encoded by a polynucleotide comprising the nucleic acid that is at least about 80%, at least about 85%, at least about 90%, at least about 95%, at least about 96%, at least about 98%, at least about 99%, or 100% identical to the nucleic acid sequence of SEQ ID NO:37. In some embodiments, the isolated antibody comprises a heavy chain comprising the amino acid sequence of SEQ ID NO:38 or 39. In some embodiments, the isolated antibody comprises a light chain encoded by a polynucleotide comprising the nucleic acid that is at least about 80%, at least about 85%, at least about 90%, at least about 95%, at least about 96%, at least about 98%, at least about 99%, or 100% identical to the nucleic acid sequence of SEQ ID NO:40. In some embodiments, the isolated antibody comprises a light chain comprising the amino acid sequence of SEQ ID NO:41 or 42.

In various embodiment, an antibody provided herein further comprises a detectable label, and a detectable label can be selected from the group consisting of a fluorescent label, a photochromic compound, a proteinaceous fluorescent label, a magnetic label, a radiolabel, and a hapten. When a fluorescent label is desired the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In specific embodiments a fluorescent label can be R-Phycoerythrin (PE) or Allophycocyanin (APC).

Also provided herein is a composition comprising an antibody provided herein and optionally a pharmaceutically acceptable carrier or vehicle.

Provided herein are polynucleotides encoding the heavy chain of an isolated antibody of an antibody provided herein. Further, polynucleotides encoding the light chain of an isolated antibody of an antibody provided herein are also provided. Vectors comprising a polynucleotide encoding the heavy chain of an isolated antibody of an antibody provided herein, and encoding the light chain of an isolated antibody of an antibody provided herein are also provided. Cells comprising such vectors are also provided, and in various embodiments a cell comprises a cell selected from the group consisting of a CHO cell, a Sp2/0 cell, a rabbit cell and an *E. coli* cell.

In some embodiments, the polynucleotide comprises the nucleic acid sequence of SEQ ID NO:37 or 40. In some embodiments, the polynucleotide encodes a polypeptide comprising the amino acid sequence of SEQ ID NO:38, 39, 41 or 42.

Methods of making an isolated antibody provided herein are also provided and can comprise incubating a cell provided herein under suitable conditions.

A method of determining a number of cells expressing a 4G7 derived scFv is provided and can comprise contacting a sample with an isolated antibody that specifically binds the 4G7 derived scFv conjugated to a detectable label and determining the number of cells expressing the 4G7 derived scFv in the sample. In embodiments, the isolated antibody that specifically binds the 4G7 derived scFv is an antibody provided herein or a humanized form thereof.

Also provided is a method of determining a number of cells presenting a polypeptide comprising an anti-CD19 scFv derived from 4G7, wherein the method comprises: (a) providing a sample comprising cells known or suspected to be presenting a polypeptide comprising an anti-CD19 scFv derived from 4G7; (b) contacting the sample with the isolated antigen binding molecule provided herein or a humanized form thereof under conditions that permit binding of the polypeptide and the antigen binding molecule; and (c) determining the number of cells presenting the polypeptide in the sample.

Provided herein is a method of determining the presence or absence of a polypeptide comprising an anti-CD19 scFv derived from 4G7, wherein the method comprises: (a) providing a sample known or suspected to comprise a polypeptide an anti-CD19 scFv derived from 4G7; (b) contacting the sample with an isolated antigen binding molecule provided herein or a humanized form thereof under conditions that permit binding of the polypeptide and the antigen binding molecule; and (c) detecting the presence or absence of a polypeptide:antigen binding molecule complex. In an embodiment of the method the sample is a formalin-fixed sample. In another embodiment the 4G7 derived scFv is a component of a chimeric antigen receptor (CAR), and in further embodiments the cell expressing a 4G7 derived scFv CAR is an immune cell selected from the group consisting of CD8+ T cells, CD4+ T cells, tumor infiltrating lymphocytes (TILs), NK cells, TCR-expressing cells, dendritic cells, and NK-T cells. In some embodiments, the isolated antigen binding molecule is detectably labeled, and the detectable label can be selected from the group consisting of a fluorescent label, a photochromic compound, a proteinaceous fluorescent label, a magnetic label, a radiolabel, and a hapten. When the detectable label is a fluorescent label, the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In a specific embodiment the fluorescent label is R-Phycoerythrin (PE) or Allophycocyanin (APC). In some embodiments the cell expressing a 4G7 derived scFv CAR is an immune cell the immune cell is a T cell, which can be disposed in vitro or in vivo. In embodiments the T cell is disposed in blood, extracted tissue, tissue grown ex vivo or cell culture media. In one embodiment the T cell is an autologous T cell. In another embodiment the T cell is an allogenic T cell.

BRIEF DESCRIPTION OF THE DRAWINGS

FIG. 4A shows a line graph of % CAR+ cells detectable by soluble CD19-Fc fusion protein after pretreatment with either the anti-Id antibody or an irrelevant isotype control. FIGS. 4B and 4C show flow cytometry plots from FIG. 4A of increasing concentration of idiotype Ab A8 (E2153.2H8.A8) (FIG. 4B) and unconjugated mouse IgG1 Isotype control (FIG. 4C). FIGS. 4D and 4E show the ability of the anti-Id m4G7 (A8) to block tumor cell lysis at 5:1 and 10:1 E:T ratios, respectively.

DETAILED DESCRIPTION

Figure 1:
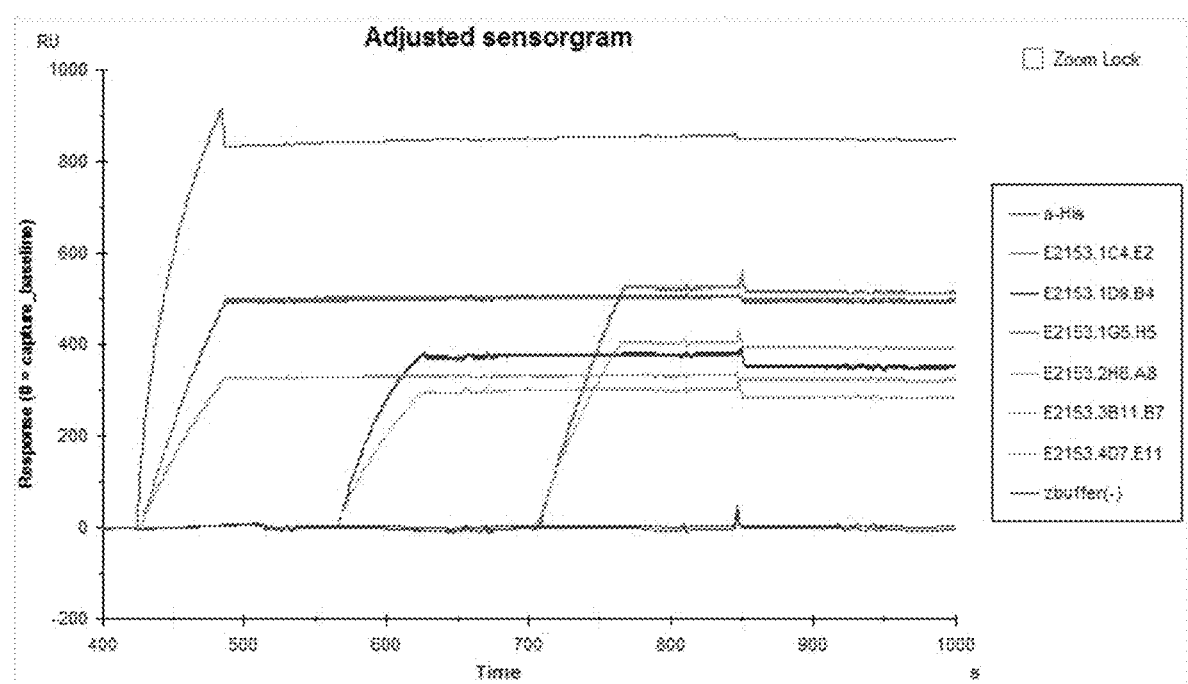
FIG. 1 shows a sensorgram plot showing capture of all biotinylated anti-Id sub-clones (E2153.1C4.E2 "Clone E2", E2153.1D9.B4 "Clone B4", E2153.1G5.H5 "Clone H5", E2153.2H8.A8 "Clone A8", E2153.3B11.B7 "Clone B7", E2153.4D7.E11 "Clone E11") to CAPture chip surface.

The scFv portion of some chimeric antigen receptors (CARs), e.g., at least UCART19, ALLO-501 and ALLO-501A, is derived from the mouse anti-human CD19 antibody clone 4G7. The present disclosure provides reagents to detect anti-CD19 CARs comprising an scFv portion derived from antibody clone 4G7 (e.g., UCART19 and ALLO-501). Disclosed herein are anti-idiotype antibodies (anti-Id) antibodies that specifically bind to anti-CD19 clone 4G7 and anti-CD19 molecules derived from 4G7. Anti-Id antibodies to 4G7 derived molecules disclosed herein demonstrate specific high affinity binding to chimeric antigen receptors (CAR) comprising a 4G7 derived scFv (e.g., UCART19, ALLO-501 and ALLO-501A). One unlimiting example of the 4G7 derived scFv comprises the amino acid sequence of SEQ ID NO:36.

When conjugated to a bright fluorochrome, the anti-id antibodies disclosed herein stain cells expressing chimeric antigen receptors (CAR) comprising a 4G7 derived scFv (e.g., UCART19, ALLO-501 and ALLO-501A) with a high MFI and low background. The antibodies described herein can be used in a method to detect anti-CD19 CAR expression. These antibodies can be used to identify, e.g., UCART19 and ALLO-501 by both flow cytometry and immunohistochemistry. These antibodies can also be used in the context of non-clinical research studies, manufacturing of immune cells comprising a 4G7 derived scFv (e.g., UCART19 and ALLO-501), as a clinical flow-based pharmacokinetic reagent and in clinical immunogenicity studies.

4G7 is a CD19 monoclonal antibody that recognizes CD19. Single chain variable fragments (scFv) formed from 4G7 comprise the targeting component of some chimeric antigen receptors (CARs) (See WO2014184143A1, U.S. 62/839,455, filed on Apr. 26, 2019, and U.S. 63/005,041, filed on Apr. 3, 2020.). In some embodiments, the scFv derived from the CD19 monoclonal antibody 4G7, comprises a part of the CD19 monoclonal antibody 4G7 immunoglobulin gamma 1 heavy chain (GenBank: CAD88275.1; SEQ ID NO: 34) and a part of anti-CD19 monoclonal antibody 4G7 immunoglobulin kappa light chain (GenBank: CAD88204.1; SEQ ID NO: 35), linked together by a flexible linker. (Peipp M., D. Saul, et al., 2004. Efficient eukaryotic expression of fluorescent scFv fusion proteins directed against CD antigens for FACS applications. *J. Immunol. Methods* 285: 265-280). In some embodiments, the scFv comprises the variable fragments of the anti-CD19 monoclonal antibody 4G7 immunoglobulin gamma 1 heavy chain and the variable fragments of the anti-CD19 monoclonal antibody 4G7 immunoglobulin kappa light chain linked together by a flexible linker.

The anti-CD19 monoclonal antibody 4G7 immunoglobulin gamma 1 heavy chain comprises the amino acid sequence:

MEWSWIFLFLLSGTAGVHSEVQLQQSGPELIKPGASVKMSCKASGYTFTSY

VMHWVKQKPGQGLEWIGYINPYNDGTKYNEKFKGKATLTSDKSSSTAYMEL

SSLTSEDSAVYYCARGTYYYGSRVFDYWGQGTTLTVSSAKTTPPSVYPLAP

GSAAQTNSMVTLGCLVKGYFPEPVTVTWNSGSLSSGVHTFPAVLQSDLYTL

SSSVTVPSSTWPSETVTCNVAHPASSTKVDKKIVPRDCGCKPCICTVPEVS

SVFIFPPKPKDVLTITLTPKVTCVVVDISKDDPEVQFSWFVDDVEVHTAQT

QPREEQFNSTFRSVSELPIMHQDWLNGKEFKCRVNSAAFPAPIEKTISKTK

GRPKAPQVYTIPPPKEQMAKDKVSLTCMITDFFPEDITVEWQWNGQPAENY

KNTQPIMDTDGSYFVYSKLNVQKSNWEAGNTFTCSVLHEGLHNHHTEKSLS

HSPGK
(SEQ ID NO: 34, underlined is a signal sequence, VH is in bold also shown in SEQ ID NO:)

The anti-CD19 monoclonal antibody 4G7 immunoglobulin kappa light chain comprises the amino acid sequence:

MRCLAEFLGLLVLWIPGAIGDIVMTQAAPSIPVTPGESVSISCRSSKSLLN

SNGNTYLYWFLQRPGQSPQLLIYRMSNLASGVPDRFSGSGSGTAFTLRISR

VEAEDVGVYYCMQHLEYPFTFGAGTKLELKRADAAPTVSIFPPSSEQLTSG

GASVVCFLNNFYPKDINVKWKIDGSERQNGVLNSWTDQDSKDSTYSMSSTL

TLTKDEYERHNSYTCEATHKTSTSPIVKSFNRNEC
(SEQ ID NO: 35, underlined is a signal sequence, VL is in bold)

An exemplary 4G7 derived scFv comprises the amino acid sequence:

EVQLQQSGPELIKPGASVKMSCKASGYTFTSYVMHWVKQKPGQGLEWIGYI

NPYNDGTKYNEKFKGKATLTSDKSSSTAYMELSSLTSEDSAVYYCARGTYY

YGSRVFDYWGQGTTLTVSSGGGGSGGGGSGGGGSDIVMTQAAPSIPVTPGE

SVSISCRSSKSLLNSNGNTYLYWFLQRPGQSPQLLIYRMSNLASGVPDRFS

GSGSGTAFTLRISRVEAEDVGVYYCMQHLEYPFTFGAGTKLELK
(SEQ ID NO: 36, VH CDR1, CDR2, CDR3, and VL CDR1, CDR2 and CDR3 are each underlined)

In some embodiments, the scFv comprises a part of amino acid sequences of SEQ ID NO: 34 and/or SEQ ID NO: 35. In some embodiments, the scFv comprises a part of amino acid sequences of SEQ ID NO: 34 and/or SEQ ID NO: 35, with or without the signal sequence. In some embodiments, the scFv comprises at least 50%, at least 60%, at least 70%, at least 80%, at least 90%, at least 95%, at least 97% or at least 99% sequence identity with the variable region of amino acid sequence of SEQ ID NO: 34 and/or SEQ ID NO: 35. In some embodiments, the scFv comprises at least 50%, at least 60%, at least 70%, at least 80%, at least 90%, at least 95%, at least 97%, at least 99%, or 100% sequence identity with the amino acid sequence of SEQ ID NO: 36. Disclosed herein are antigen binding molecules, including antibodies, that specifically bind to the anti-CD19 scFv derived from 4G7, as well as molecules comprising these sequences and cells presenting such molecules. Humanized forms of the antigen binding molecules also form as aspect of the disclosure. Applications and uses of these antigen binding molecules are also disclosed.

I. Antigen Binding Molecules and Polynucleotides Encoding Same

An "antigen binding domain" as used herein means any polypeptide that binds a specified target antigen, for example the specified target antigen can be the CD19 protein or fragment thereof (referred to interchangeably herein as a "CD19 antigen", "CD19 target antigen", or "CD19 target"). In the context of an anti-idiotype antibody of the present disclosure, the target antigen is an antigen binding molecule that specifically binds CD19 (e.g., antibody clone 4G7 and antigen binding molecules derived from or related to 4G7, including scFv's).

In some embodiments, the antigen binding domain binds to a CD19 antigen on a tumor cell. In some embodiments, the antigen binding domain binds to a CD19 antigen on a cell involved in a hyperproliferative disease or to a viral or bacterial antigen.

Antigen binding domains include, but are not limited to, antibody binding regions that are immunologically functional fragments. The term "immunologically functional fragment" (or "fragment") of an antigen binding domain is a species of antigen binding domain comprising a portion (regardless of how that portion is obtained or synthesized) of an antibody that lacks at least some of the amino acids present in a full-length chain, but which is still capable of specifically binding to a target antigen. Such fragments are biologically active in that they bind to the target antigen and can compete with other antigen binding domains, including intact antibodies, for binding to a given epitope. In some embodiments, the fragments are neutralizing fragments. In some embodiments, the fragments can block or reduce the activity of an anti-CD19 CAR (e.g., a blocking effect). In some embodiments, the fragments can antagonize the activity of an anti-CD19 CAR.

In specific embodiments, an anti-Id antibody of the instant disclosure is an antibody identified herein as Clones E2, B4, A8, E11 and each comprises the heavy and light chain amino acid, variable, CDR sequences and nucleotide sequences encoding such sequences, as provided and labeled herein.

Immunologically functional immunoglobulin fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multispecific antigen binding domains, and single-chain antibodies. These fragments can be derived from any mammalian source, including but not limited to human, mouse, rat, camelid or rabbit. As will be appreciated by one of skill in the art, an antigen binding domain can include non-protein components.

The variable regions typically exhibit the same general structure of relatively conserved framework regions (FR) joined by the 3 hypervariable regions (CDRs). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3.

In some embodiments, antigen binding domains comprise one or more complementarity binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody of fragment thereof, including one or more of the complementarity determining regions (CDRs) thereof. In some embodiments, the antigen binding domain is a single chain variable fragment (scFv), comprising light chain CDRs CDR1, CDR2 and CDR3, and heavy chain CDRs CDR1, CDR2 and CDR3.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, or the AbM scheme (Antibody Modeling program, Oxford Molecular).

Accordingly, in some embodiments, the CDRs of the anti-idiotype antibodies presented herein are numbered according to the Kabat numbering scheme. In other embodiments, the CDRs of the anti-idiotype antibodies presented herein are numbered according to the Chothia numbering scheme. In other embodiments, the CDRs of the anti-idiotype antibodies presented herein are numbered according to the contact numbering scheme. In other embodiments, the CDRs of the anti-idiotype antibodies presented herein are numbered according to the AbM numbering scheme.

Humanized antibodies are described herein and can be prepared by known techniques. In some embodiments, a humanized monoclonal antibody comprises the variable domain of an anti-Id antibody (or all or part of the antigen binding site thereof) and a constant domain derived from a human antibody. Alternatively, a humanized antibody fragment can comprise an antigen binding site of a murine or rabbit monoclonal antibody and a variable domain fragment (lacking the antigen binding site) derived from a human antibody. Procedures for the production of engineered monoclonal antibodies include those described in, e.g., Riechmann et al., (1988) *Nature* 332:323, Liu et al., (1987) *Proc. Nat. Acad. Sci. USA* 84:3439, Larrick et al., (1989) *Bio/Technology* 7:934, and Winter et al., (1993) TIPS 14:139. In some embodiments, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J.* 9:133-39; Tamura et al., (2000) *J. Immunol.* 164:1432-41; Zhang et al., (2005) *Mol. Immunol.* 42(12): 1445-1451; Hwang et al., *Methods.* (2005) 36(1):35-42; Dall'Acqua et al., (2005) *Methods* 36(1):43-60; and Clark, (2000) *Immunology Today* 21(8):397-402.

Variants of the anti-idiotype antibodies are also within the scope of the disclosure, e.g., variable light and/or variable heavy chains that each have at least 70-80%, 80-85%, 85-90%, 90-95%, 95-97%, 97-99%, or above 99% identity to the amino acid sequences of the antigen binding domain sequences described herein. In some embodiments, the anti-idiotype antibody is at least about 75%, at least about 85%, at least about 85%, at least about 90%, at least about 95%, at least about 96%, at least about 97%, at least about 98%, at least about 99%, or 100% identical to a heavy chain variable region sequence provided in Table 1a and/or a light chain variable sequence provided in Table 1b.

In some instances, such molecules include at least one heavy chain and one light chain, whereas in other instances the variant forms contain two variable light chains and two variable heavy chains (or subparts thereof). A skilled artisan will be able to determine suitable variants of the anti-idiotype antibodies as set forth herein using well-known techniques. In certain embodiments, one skilled in the art can identify suitable areas of the molecule that can be changed without destroying activity by targeting regions not believed to be important for activity.

An anti-Id antibody of the present disclosure can also be a fully human monoclonal antibody. Fully human monoclonal antibodies can be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

An anti-Id antibody that specifically binds to anti-CD19 clone 4G7 and anti-CD19 molecules derived from 4G7 is said to be "selective" when it binds to one target more tightly than it binds to a second target.

An anti-Id antibody that specifically binds to anti-CD19 clone 4G7 and anti-CD19 molecules derived from 4G7 is said to "specifically bind" its target antigen (e.g., mouse 4G7 and molecules derived from 4G7) when the dissociation constant (Kd) is ~1 nM. The antigen binding domain specifically binds antigen with "high affinity" when the Kd is 1-5 nM, and with "very high affinity" when the Kd is 0.1-0.5 nM. In one embodiment, the antigen binding domain has a Kd of ~1 nM. In one embodiment, the off-rate is $<1\times10^{-5}$. In other embodiments, the antigen binding domains will bind to mouse 4G7 and molecules derived from 4G7 with a Kd of between about $1\times10^{-7}$ M and $1\times10^{-12}$ M, and in yet another embodiment the antigen binding domains will bind with a Kd between about $1\times10^{-5}$ and $1\times10^{-12}$.

As provided herein, the anti-Id antibodies of the present disclosure specifically bind mouse 4G7 and molecules derived from 4G7 (e.g., murine 4G7, humanized 4G7, 4G7 derived CARs). In certain embodiments, the anti-Id antibodies of the present disclosure bind mouse 4G7 and molecules derived from 4G7 with a KD of less than $1\times10^{-6}$ M, less than $1\times10^{-7}$ M, less than $1\times10^{-8}$ M, or less than $1\times10^{-9}$ M. In one particular embodiment, the anti-Id antibodies bind mouse 4G7 and molecules derived from 4G7 with a KD of less than $1\times10^{-7}$ M. In another embodiment, the anti-Id antibodies bind mouse 4G7 and molecules derived from 4G7 with a KD of less than $1\times10^{-8}$ M. In some embodiments, the anti-Id antibodies bind mouse 4G7 and molecules derived from 4G7 with a Kd of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-1}$ M. In certain embodiments, the Kd is calculated as the quotient of $K_{off}/K_{on}$, and the $K_{on}$ and $K_{off}$ are determined using a monovalent antibody, such as a Fab fragment, as measured by, e.g., BIAcore® surface plasmon resonance technology. In other embodiments, the Kd is calculated as the quotient of $K_{off}/K_{on}$, and the $K_{on}$ and $K_{off}$ are determined using a bivalent antibody, such as a Fab fragment, as measured by, e.g., BIAcore® surface plasmon resonance technology.

In some embodiments, the anti-Id antibodies bind mouse 4G7 and molecules derived from 4G7 with an association rate ($k_{on}$) of less than $1\times10^{-4}$ M$^{-1}$ s$^{-1}$, less than $2\times10^{-4}$ M$^{-1}$ s$^{-1}$, less than $3\times10^{-4}$ M$^{-1}$ s$^{-1}$, less than $4\times10^{-4}$ M$^{-1}$ s$^{-1}$, less than $5\times10^{-4}$ M$^{-1}$ s$^{-1}$, less than $7\times10^{-4}$ M$^{-1}$ s$^{-1}$ less than $8\times10^{-4}$ M$^{-1}$ s$^{-1}$ less than $9\times10^{-4}$ M$^{-1}$ s$^{-1}$ less than $1\times10^{-5}$ M$^{-1}$ s$^{-1}$ less than $2\times10^{-5}$ M$^{-1}$ s$^{-1}$ less than $3\times10^{-5}$ M$^{-1}$ s$^{-1}$ less than $4\times10^{-5}$ M$^{-1}$ s$^{-1}$ less than $5\times10^{-5}$ M$^{-1}$ s$^{-1}$ less than $6\times10^{-5}$ M$^{-1}$ s$^{-1}$, less than $7\times10^{-5}$ M$^{-1}$ s$^{-1}$, less than $8\times10^{-5}$ M$^{-1}$ s$^{-1}$, less than $9\times10^{-5}$ M$^{-1}$ s$^{-1}$, less than $1\times10^{-6}$ M$^{-1}$ s$^{-1}$, less than $2\times10^{-6}$ M$^{-1}$ s$^{-1}$ less than $3\times10^{-6}$ M$^{-1}$ s$^{-1}$, less than $4\times10^{-6}$ M$^{-1}$ s$^{-1}$ less than $5\times10^{-6}$ M$^{-1}$ s$^{-1}$ less than $6\times10^{-6}$ M$^{-1}$ s$^{-1}$ less than $7\times10^{-6}$ M$^{-1}$ s$^{-1}$ less than $8\times10^{-6}$ M$^{-1}$ s$^{-1}$, less than $9\times10^{-6}$ M$^{-1}$ s$^{-1}$, or less than $1\times10^{-7}$ M$^{-1}$ s$^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the anti-Id antibodies bind mouse 4G7 and molecules derived from 4G7 with an dissociation rate ($k_{off}$) of less than $1\times10^{-2}$ s$^{-1}$, less than $2\times10^{-2}$ s$^{-1}$, less than $3\times10^{-2}$ s$^{-1}$, less than $4\times10^{-2}$ s$^{-1}$, less than $5\times10^{-2}$ s$^{-1}$, less than $6\times10^{-2}$ s$^{-1}$, less than $7\times10^{-2}$ s$^{-1}$, less than $8\times10^{-2}$ s$^{-1}$, less than $9\times10^{-2}$ s$^{-1}$, less than $1\times10^{-3}$ s$^{-1}$, less than $2\times10^{-3}$ s$^{-1}$, less than $3\times10^{-3}$ s$^{-1}$, less than $4\times10^{-3}$ s$^{-1}$, less than $5\times10^{-3}$ s$^{-1}$, less than $6\times10^{-3}$ s$^{-1}$, less than $7\times10^{-3}$ s$^{-1}$, less than $8\times10^{-3}$ s$^{-1}$, less than $9\times10^{-3}$ s$^{-1}$, less than $1\times10^{-4}$ s$^{-1}$, less than $2\times10^{-4}$ s$^{-1}$, less than $3\times10^{-4}$ s$^{-1}$, less than $4\times10^{-4}$ s$^{-1}$, less than $5\times10^{-4}$ s$^{-1}$, less than $6\times10^{-4}$ s$^{-1}$ less than $7\times10^{-4}$ s$^{-1}$, less than $8\times10^{-4}$ s$^{-1}$, less than $9\times10^{-4}$ s$^{-1}$, less than $1\times10^{-5}$ s$^{-1}$, or less than $5\times10^{-4}$ s$^{-1}$. In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

Provided herein are anti-idiotype antibodies (anti-Id) antibodies that specifically bind to anti-CD19 clone 4G7 and antigen binding molecules derived from 4G7, comprising a variable heavy chain (VH), wherein the amino acid sequence or polynucleotide sequence of the VH is selected from the VH sequences presented in Table 1a.

TABLE 1a

Heavy Chain Variable Regions (VH)

| Clone | VH Sequence | SEQ ID NO: |
|---|---|---|
| Amino Acid Sequence | | |
| A8 | QVQLQQSGAELVKPGASVKVSCKAFGYTFTTYPIEWMRQN HGKSLEWIGNFHPYNDDTRYNEKFKDKAKLTVEKSSSTVY LELSRLTYDDSAVYYCTRGNDYDLYGMDYWGQGTSVTVSS | 1 |
| B4 | QVQLQQSGAELVRPGTSVKVSCKASGYAFTNYLIEWIKQR PGQGLEWIGVINpGSGGINYNEKFKGKATLTSDKSSSTAY MQLSSLTSDDSAVYFCARWLDYDWFAYWGQGTLVTVSA | 2 |
| E11 | QVQLQQSGAELVRPGTSVKVSCKASGYAFTNYLIEWVKQR PGQGLEWIGVITpGSGGSNYNEKFKGKATLTADKSSSTAY MQLSSLTSDDSAVYFCARWLDYDWFAYWGQGTLVTVSA | 3 |
| E2 | QVQLQQSGAELVKPGASVKVSCKAFGYTFTTYPIEWMRQN HGKSLEWIGNFHPyNDDTRYNEKFKDKAKLTVEKSSSTVY LELSRLTYDDSAVYYCTRGNDYd1YGMDYWGQGTSVTVSS | 1 |
| Polynucleotide Sequence | | |
| A8 | CAGGTTCAGCTGCAGCAGTCTGGGGCTGAGCTGGTGAAGC CTGGGGCCTCAGTGAAGGTGTCCTGCAAGGCTTTTGGCTA CACCTTCACTA CCTATCCAATAGAGTGGATGAGGCAGAA TCATGGAAAGAGCCTAGAGTGGATTGGAAATTTTCATCCT TACAATGATGATACTAGGTACAATGAAAAATTCAAGGACA AGGCCAAATTGACTGTAGAAAAATCCTCTAGCACAGTCTA CTTGGAGCTCAGCCGATTAACATATGATGACTCTGCTGTT TATTACTGTACAAGGGGGAATGATTACGACCTCTATGGTA TGGACTACTGGGGTCAAGGAACCTCAGTCACCGTCTCCTC A | 4 |
| B4 | CAGGTCCAGCTGCAGCAGTCTGGAGCTGAACTGGTAAGGC CTGGGACTTCAGTGAAGGTGTCCTGCAAGGCTTCTGGATA CGCCTTCACTAATTATTTGATAGAGTGGATAAAGCAGAGG CCTGGACAGGGCCTTGAGTGGATTGGAGTGATTAATCCTG GAAGTGGTGGTATTAATTATAATGAGAAGTTCAAGGGCAA GGCAACACTGACTTCAGACAAATCCTCCAGCACTGCCTAC ATGCAGCTCAGCAGCCTGACATCTGATGACTCTGCGGTCT | 5 |

TABLE 1a-continued

Heavy Chain Variable Regions (VH)

| Clone | VH Sequence | SEQ ID NO: |
|---|---|---|
| | ATTTCTGTGCAAGATGGCTTGATTACGACTGGTTTGCTTA CTGGGGCCAAGGGACTCTGGTCACTGTCTCTGCA | |
| E11 | CAGGTCCAGCTGCAGCAGTCTGGAGCTGAGCTGGTAAGGC CTGGGACTTCAGTGAAGGTGTCCTGCAAGGCCTCTGGGTA CGCCTTCACTAATTATTTGATAGAGTGGGTAAAGCAGAGG CCTGGACAGGGCCTAGAGTGGATTGGAGTGATTACTCCTG GAAGTGGCGGTTCTAACTACAATGAGAAGTTCAAGGGCAA GGCAACACTGACTGCAGACAAATCCTCCAGCACTGCCTAC ATGCAGCTCAGCAGCCTGACATCTGATGACTCTGCGGTCT ACTTCTGTGCAAGATGGCTTGATTACGACTGGTTTGCTTA CTGGGGCCAAGGGACTCTGGTCACTGTCTCTGCA | 6 |
| E2 | CAGGTTCAGCTGCAGCAGTCTGGGGCTGAGCTGGTGAAGC CTGGGGCCTCAGTGAAGGTGTCCTGCAAGGCTTTTGGCTA CACCTTCACTACCTATCCAATAGAGTGGATGAGGCAGAAT CATGGAAAGAGCCTAGAGTGGATTGGAAATTTTCATCCTT ACAATGATGATACTAGGTACAATGAAAAATTCAAGGACAA GGCCAAATTGACTGTAGAAAAATCCTCTAGCACAGTCTAC TTGGAGCTCAGCCGATTAACATATGATGACTCTGCTGTTT ATTACTGTACAAGGGGAATGATTACGACCTCTATGGTAT GGACTACTGGGGTCAAGGAACCTCAGTCACCGTCTCCTCA | 4 |

Provided herein are anti-idiotype antibodies (anti-Id) antibodies that specifically bind to anti-CD19 clone 4G7, comprising a variable light chain (VL), wherein the amino acid sequence or polynucleotide sequence of the VL is selected from the VL sequences presented in Table 1b.

TABLE 1b

Light Chain Variable Regions

| Clone | VL Sequence | SEQ ID NO: |
|---|---|---|
| Amino Acid Sequence | | |
| A8 | DIKMTQSPSSMYASLGERVTITCKASQDINTYLTWFQQKP GKSPKTLIYRANRLVDGVPSRFSGSGSGQDYSLTISSLEY EDMGIYYCLQCDDFPLTFGAGTKLELK | 7 |
| B4 | DIKMTQFPSSMYASVGERVTITCKASQDINSYLSWFQQKP GKSPKTLIYRANRLVDGVPSRFSGSGSGQDYSLTISSLEY EDMGIYYCLQCDEFPFTFGGGTKLEIK | 8 |
| E11 | DIKMTQSPSSMYASLGERVTITCKASQDINSYLSWFQQKP GKSPKTLIYRANRLVDGVPSRFSGSGSGQDYSLTISSLEY EDMGIYYCRQCDEFPSTFGGGTKLEIK | 9 |
| E2 | DIKMTQFPSSMYASLGERVTITCKASQDINTYLTWFQQKP GKSPKTLIYRANRLVDGVPSRFSGSGSGQDYSLTISSLEY EDMGIYYCLQCDDFPLTFGAGTKLELK | 10 |
| Polynucleotide Sequence | | |
| A8 | GACATCAAGATGACCCAGTCTCCATCTTCCATGTATGCAT CTCTAGGAGAGAGTCACTATCACTTGCAAGGCGAGTCA GGACATTAATACCTATTTAACCTGGTTCCAGCAGAAACCA GGGAAATCTCCTAAGACCCTGATCTATCGTGCAAACAGAT TGGTAGATGGGGTCCCATCAAGGTTCAGTGGCAGTGGATC TGGGCAAGATTATTCTCTCACCATCAGCAGCCTGGAGTAT GAAGATATGGGAATTTATTATTGTCTACAGTGTGATGATT TTCCGCTCACGTTCGGTGCTGGGACCAAGCTGGAGCTGAA A | 11 |
| B4 | GACATCAAGATGACCCAGTTTCCATCTTCCATGTATGCAT CTGTAGGAGAGAGTCACTATCACTTGCAAGGCGAGTCA GGACATTAATAGCTATTTAAGCTGGTTCCAGCAGAAACCA GGGAAATCTCCTAAGACCCTGATTTATCGTGCAAACAGAT | 12 |

TABLE 1b-continued

Light Chain Variable Regions

| Clone | VL Sequence | SEQ ID NO: |
|---|---|---|
| | TGGTAGATGGGGTCCCATCAAGGTTCAGTGGCAGTGGATC TGGGCAAGATTATTCTCTCACCATCAGCAGCCTGGAGTAT GAAGATATGGGAATTTATTATTGTCTACAGTGTGATGAGT TTCCGTTCACGTTCGGAGGGGGGACCAAGCTGGAAATAAA A | |
| E11 | GACATCAAGATGACCCAGTCTCCATCTTCCATGTATGCAT CTCTAGGAGAGAGTCACTATCACTTGCAAGGCGAGTCA GGACATTAATAGCTATTTAAGCTGGTTCCAGCAGAAACCA GGGAAATCTCCTAAGACCCTGATCTATCGTGCAAACAGAT TGGTAGATGGGGTCCCATCAAGGTTCAGTGGCAGTGGATC TGGGCAAGATTATTCTCTCACCATCAGCAGCCTGGAGTAT GAAGATATGGGAATTTATTATTGTCGACAGTGTGATGAGT TTCCGTCCACGTTCGGAGGGGGGACCAAGCTGGAAATAAA A | 13 |
| E2 | GACATCAAGATGACCCAGTTTCCATCTTCCATGTATGCAT CTCTAGGAGAGAGTCACTATCACTTGCAAGGCGAGTCA GGACATTAATACCTATTTAACCTGGTTCCAGCAGAAACCA GGGAAATCTCCTAAGACCCTGATCTATCGTGCAAACAGAT TGGTAGATGGGGTCCCATCAAGGTTCAGTGGCAGTGGATC TGGGCAAGATTATTCTCTCACCATCAGCAGCCTGGAGTAT GAAGATATGGGAATTTATTATTGTCTACAGTGTGATGATT TTCCGCTCACGTTCGGTGCTGGGACCAAGCTGGAGCTGAA A | 14 |

Provided herein are anti-idiotype antibodies (anti-Id) antibodies that specifically bind to anti-CD19 clone 4G7 and antigen binding molecules derived from 4G7, wherein anti-Id antibodies comprise a variable heavy chain (VH) and a variable light chain (VL), wherein the amino acid sequence or polynucleotide sequence of the VH is selected from the V sequences presented in Table 1a; and wherein the amino acid sequence or polynucleotide sequence of the VL is selected from the VL sequences presented in Table 1b.

In some embodiments, the anti-idiotype antibodies (anti-Id) antibodies that specifically bind to anti-CD19 clone 4G7 and antigen binding molecules derived from 4G7, comprise a VH CDR 1, CDR2, and CDR3 of a VH sequence presented in Table 1a. In some embodiments, the VH CDR 1, CDR2, and CDR3 are selected from a CDR sequence presented in Table 1c.

TABLE 1c

Heavy Chain CDRs

| Clone | CDR1 VH Sequence (Chothia) | SEQ ID NO: | CDR1 VH Sequence (Kabat) | SEQ ID NO: |
|---|---|---|---|---|
| A8 | GYTFTTY | 15 | TYPIE | 21 |
| B4 | GYAFTNY | 24 | NYLIE | 29 |
| E11 | GYAFTNY | 24 | NYLIE | 29 |
| E2 | GYTFTTY | 15 | TYPIE | 21 |

| Clone | CDR2 VH Sequence (Chothia) | SEQ ID NO: | CDR2 VH Sequence (Kabat) | SEQ ID NO: |
|---|---|---|---|---|
| A8 | HPYNDD | 16 | NFHPYNDDTRYNEKFKD | 22 |
| B4 | NPGSGG | 25 | VINPGSGGINYNEKFKG | 30 |

TABLE 1c-continued

Heavy Chain CDRs

| | | | | |
|---|---|---|---|---|
| E11 | TPGSGG | 31 | VI<u>TPGSGG</u>SNYNEKFKG | 33 |
| E2 | HPYNDD | 16 | NF<u>HPYNDD</u>TRYNEKFKD | 22 |

| Clone | CDR3 VH Sequence (Chothia) | SEQ ID NO: | CDR3 VH Sequence (Kabat) | SEQ ID NO: |
|---|---|---|---|---|
| A8 | GNDYDLYGMDY | 17 | GNDYDLYGMDY | 23 |
| B4 | WLDYDWFAY | 26 | WLDYDWFAY | 26 |
| E11 | WLDYDWFAY | 26 | WLDYDWFAY | 26 |
| E2 | GNDYDLYGMDY | 17 | GNDYDLYGMDY | 23 |

In some embodiments, the anti-idiotype antibodies (anti-Id) antibodies that specifically bind to anti-CD19 clone 4G7 and antigen binding molecules derived from 4G7, comprise a VL CDR 1, CDR2, and CDR3 of a VL sequence presented in Table 1b. In some embodiments, the VH CDR 1, CDR2, and CDR3 are selected from a CDR sequence presented in Table 1d.

TABLE 1d

Light Chain CDRs

| Clone | CDR1 VL Sequence (Kabat and Chothia) | SEQ ID NO: |
|---|---|---|
| A8 | KASQDINTYLT | 18 |
| B4 | KASQDINSYLS | 27 |
| E11 | KASQDINSYLS | 27 |
| E2 | KASQDINTYLT | 18 |

| Clone | CDR2 VL Sequence (Kabat and Chothia) | SEQ ID NO: |
|---|---|---|
| A8 | RANRLVD | 19 |
| B4 | RANRLVD | 19 |
| E11 | RANRLVD | 19 |
| E2 | RANRLVD | 19 |

| Clone | CDR3 VL Sequence (Kabat and Chothia) | SEQ ID NO: |
|---|---|---|
| A8 | LQCDDFPLT | 20 |
| B4 | LQCDEFPFT | 28 |
| E11 | RQCDEFPST | 32 |
| E2 | LQCDDFPLT | 20 |

The DNA and amino acid sequences of the heavy chain and light chain of clone A8 are shown below:

2153.2H8.A8 mouse IgG1 heavy chain DNA sequence (SEQ ID NO: 37)
ATGGCGTGGATCTCTATCATCCTCTTCCTAGTGGCAACAGCTATAGGTGTC

CACTCCCAGGTTCAGCTGCAGCAGTCTGGGGCTGAGCTGGTGAAGCCTGGG

GCCTCAGTGAAGGTGTCCTGCAAGGCTTTTGGCTACACCTTCACTACCTAT

CCAATAGAGTGGATGAGGCAGAATCATGGAAAGAGCCTAGAGTGGATTGGA

AATTTTCATCCTTACAATGATGATACTAGGTACAATGAAAAATTCAAGGAC

AAGGCCAAATTGACTGTAGAAAAATCCTCTAGCACAGTCTACTTGGAGCTC

AGCCGATTAACATATGATGACTCTGCTGTTTATTACTGTACAAGGGGGAAT

GATTACGACCTCTATGGTATGGACTACTGGGGTCAAGGAACCTCAGTCACC

GTCTCCTCAGCCAAAACGACACCCCCATCTGTCTATCCACTGGCCCCTGGA

TCTGCTGCCCAAACTAACTCCATGGTGACCCTGGGATGCCTGGTCAAGGGC

TATTTCCCTGAGCCAGTGACAGTGACCTGGAACTCTGGATCCCTGTCCAGC

GGTGTGCACACCTTCCCAGCTGTCCTGCAGTCTGACCTCTACACTCTGAGC

AGCTCAGTGACTGTCCCCTCCAGCACCTGGCCCAGCGAGACCGTCACCTGC

AACGTTGCCCACCCGGCCAGCAGCACCAAGGTGGACAAGAAAATTGTGCCC

AGGGATTGTGGTTGTAAGCCTTGCATATGTACAGTCCCAGAAGTATCATCT

GTCTTCATCTTCCCCCCAAAGCCCAAGGATGTGCTCACCATTACTCTGACT

CCTAAGGTCACGTGTGTTGTGGTAGACATCAGCAAGGATGATCCCGAGGTC

CAGTTCAGCTGGTTTGTAGATGATGTGGAGGTGCACACAGCTCAGACGCAA

CCCCGGGAGGAGCAGTTCAACAGCACTTTCCGCTCAGTCAGTGAACTTCCC

ATCATGCACCAGGACTGGCTCAATGGCAAGGAGTTCAAATGCAGGGTCAAC

AGTGCAGCTTTCCCTGCCCCCATCGAGAAAACCATCTCCAAAACCAAAGGC

AGACCGAAGGCTCCACAGGTGTACACCATTCCACCTCCCAAGGAGCAGATG

GCCAAGGATAAAGTCAGTCTGACCTGCATGATAACAGACTTCTTCCCTGAA

GACATTACTGTGGAGTGGCAGTGGAATGGGCAGCCAGCGGAGAACTACAAG

AACACTCAGCCCATCATGGACACAGATGGCTCTTACTTCGTCTACAGCAAG

CTCAATGTGCAGAAGAGCAACTGGGAGGCAGGAAATACTTTCACCTGCTCT

GTGTTACATGAGGGCCTGCACAACCACCATACTGAGAAGAGCCTCTCCCAC

TCTCCTGGTAAATGA 2153.2H8.A8 mouse IgG1 heavy chain amino acid sequence

<u>MAWISIILFLVATAIGVHS</u>QVQLQQSGAELVKPGASVKVSCKAFGYTFTTY

PIEWMRQNHGKSLEWIGNFHPYNDDTRYNEKFKDKAKLTVEKSSSTVYLEL

SRLTYDDSAVYYCTRGNDYDLYGMDYWGQGTSVTVSSAKTTPPSVYPLAPG

SAAQTNSMVTLGCLVKGYFPEPVTVTWNSGSLSSGVHTFPAVLQSDLYTLS

SSVTVPSSTWPSETVTCNVAHPASSTKVDKKIVPRDCGCKPCICTVPEVSS

VFIFPPKPKDVLTITLTPKVTCVVVDISKDDPEVQFSWFVDDVEVHTAQTQ

PREEQFNSTFRSVSELPIMHQDWLNGKEFKCRVNSAAFPAPIEKTISKTKG

RPKAPQVYTIPPPKEQMAKDKVSLTCMITDFFPEDITVEWQWNGQPAENYK

NTQPIMDTDGSYFVYSKLNVQKSNWEAGNTFTCSVLHEGLHNHHTEKSLSH

SPGK
(SEQ ID NO: 38, underlined is a signal sequence)

2153.2H8.A8 mouse IgG1 heavy chain amino acid sequence without the signal sequence (SEQ ID NO: 39)
QVQLQQSGAELVKPGASVKVSCKAFGYTFTTYPIEWMRQNHGKSLEWIGNF

HPYNDDTRYNEKFKDKAKLTVEKSSSTVYLELSRLTYDDSAVYYCTRGNDY

DLYGMDYWGQGTSVTVSSAKTTPPSVYPLAPGSAAQTNSMVTLGCLVKGYF

PEPVTVTWNSGSLSSGVHTFPAVLQSDLYTLSSSVTVPSSTWPSETVTCNV

AHPASSTKVDKKIVPRDCGCKPCICTVPEVSSVFIFPPKPKDVLTITLTPK

VTCVVVDISKDDPEVQFSWFVDDVEVHTAQTQPREEQFNSTFRSVSELPIM

HQDWLNGKEFKCRVNSAAFPAPIEKTISKTKGRPKAPQVYTIPPPKEQMAK

DKVSLTCMITDFFPEDITVEWQWNGQPAENYKNTQPIMDTDGSYFVYSKLN

VQKSNWEAGNTFTCSVLHEGLHNHHTEKSLSHSPGK 2153.2H8.A8 mouse kappa light chain DNA sequence (SEQ ID NO: 40)
ATGAGGACCCCTGCTCAGTTTCTTGGAATCTTGTTGCTCTGGTTTCCAGGT

ATCAAATGTGACATCAAGATGACCCAGTCTCCATCTTCCATGTATGCATCT

CTAGGAGAGAGAGTCACTATCACTTGCAAGGCGAGTCAGGACATTAATACC

TATTTAACCTGGTTCCAGCAGAAACCAGGGAAATCTCCTAAGACCCTGATC

TATCGTGCAAACAGATTGGTAGATGGGGTCCCATCAAGGTTCAGTGGCAGT

GGATCTGGGCAAGATTATTCTCTCACCATCAGCAGCCTGGAGTATGAAGAT

ATGGGAATTTATTATTGTCTACAGTGTGATGATTTTCCGCTCACGTTCGGT

GCTGGGACCAAGCTGGAGCTGAAACGGGCTGATGCTGCACCAACTGTATCC

ATCTTCCCACCATCCAGTGAGCAGTTAACATCTGGAGGTGCCTCAGTCGTG

TGCTTCTTGAACAACTTCTACCCCAAAGACATCAATGTCAAGTGGAAGATT

GATGGCAGTGAACGACAAAATGGCGTCCTGAACAGTTGGACTGATCAGGAC

AGCAAAGACAGCACCTACAGCATGAGCAGCACCCTCACGTTGACCAAGGAC

GAGTATGAACGACATAACAGCTATACCTGTGAGGCCACTCACAAGACATCA

ACTTCACCCATTGTCAAGAGCTTCAACAGGAATGAGTGTTAG 2153.2H8.A8 mouse kappa light chain amino acid sequence

MRTPAQFLGILLLWFPGIKCDIKMTQSPSSMYASLGERVTITCKASQDINT

YLTWFQQKPGKSPKTLIYRANRLVDGVPSRFSGSGSGQDYSLTISSLEYED

MGIYYCLQCDDFPLTFGAGTKLELKRADAAPTVSIFPPSSEQLTSGGASVV

CFLNNFYPKDINVKWKIDGSERQNGVLNSWTDQDSKDSTYSMSSTLTLTKD

EYERHNSYTCEATHKTSTSPIVKSFNRNEC
(SEQ ID NO: 41, underlined is a signal sequence)

2153.2H8.A8 mouse kappa light chain amino acid sequence without the signal sequence (SEQ ID NO: 42)
DIKMTQSPSSMYASLGERVTITCKASQDINTYLTWFQQKPGKSPKTLIYRA

NRLVDGVPSRFSGSGSGQDYSLTISSLEYEDMGIYYCLQCDDFPLTFGAGT

-continued
KLELKRADAAPTVSIFPPSSEQLTSGGASVVCFLNNFYPKDINVKWKIDGS

ERQNGVLNSWTDQDSKDSTYSMSSTLTLTKDEYERHNSYTCEATHKTSTSP

IVKSFNRNEC

The disclosure encompasses modifications to the anti-Id antibodies comprising the sequences shown in Tables 1a to 1d, including functionally equivalent anti-Id antibodies having modifications which do not significantly affect their properties and variants which have enhanced or decreased activity and/or affinity. For example, the amino acid sequence can be mutated to obtain an anti-Id antibody with the desired binding affinity to anti-CD19 clone 4G7 and antigen binding molecules derived from 4G7. Modification of polypeptides is routine practice in the art and thus need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or the use of chemical analogs.

Amino acid sequence insertions include amino- and/or carboxyl-terminal fusions ranginginlengthfromoneresiduetopolypeptidescontainingahundredormoreresidues, as well as intrasequence insertions of single or multiple amino acid residues. Examples of terminalinsertionsincludeanantibody-withanN-terminalmethionylresidueorthe antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antigen binding domain removed and a different residue inserted in its place. In some embodiments, sites of interest for substitutional mutagenesis include the hypervariable regions/CDRs, but FR alterations are also contemplated. Conservative substitutions are shown in Table 2 under the heading of "conservative substitutions". If such substitutions result in a change in biological activity, then more substantial changes, denominated "exemplary substitutions" in Table 2, or as further described below in reference to amino acid classes, can be introduced and the products screened.

TABLE 2

| Amino Acid Substitutions | | |
|---|---|---|
| Original Residue (naturally occurring amino acid) | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |

TABLE 2-continued

Amino Acid Substitutions

| Original Residue (naturally occurring amino acid) | Conservative Substitutions | Exemplary Substitutions |
| --- | --- | --- |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

III. Methods of Making Anti-Id Antibodies

For cloning of polynucleotides, the vector can be introduced into a host cell (an isolated host cell) to allow replication of the vector itself and thereby amplify the copies of the polynucleotide contained therein. The cloning vectors can contain sequence components generally include, without limitation, an origin of replication, promoter sequences, transcription initiation sequences, enhancer sequences, and selectable markers. These elements can be selected as appropriate by a person of ordinary skill in the art. For example, the origin of replication can be selected to promote autonomous replication of the vector in the host cell.

In certain embodiments, the present disclosure provides isolated host cells containing the vector provided herein. The host cells containing the vector can be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis, Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the disclosure provides a method of evaluating genetically engineered cells expressing a CAR which targets a CD19 protein. In some embodiments the engineered cells are evaluated after thawing cryopreserved the immune cells.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

In some aspects, the anti-Id antibodies of the present disclosure are used to quantify desired treatment amounts of cells in a composition of engineered T cells comprising a 4G7 derived CAR, e.g., an anti-CD19 CAR (such as a CAR comprising a 4G7-derived scFv such as UCART19 or ALLO-501 or ALLO-501A) or a fragment thereof. In some embodiments, the desired treatment amount is generally at least 2 cells (for example, at least 1 CD8+ central memory T cell and at least 1 CD4+ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. A clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen (CD19), lower numbers of cells, in the range of $10^6$/kilogram ($10^6$-$10^{11}$ per patient) can be administered. CAR treatments can be administered multiple times at dosages within these ranges. The cells can be autologous, allogeneic, or heterologous to the patient undergoing therapy.

The CAR expressing cell populations of the present disclosure can be administered either alone, or as a pharmaceutical composition in combination with diluents and/or with other components such as TL-2 or other cytokines or cell populations. Pharmaceutical compositions of the present disclosure can comprise a CAR or TCR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure can be formulated for intravenous administration. The pharmaceutical compositions (solutions, suspensions or the like), can include one or more of the following: sterile diluents such as water for injection, saline solution such as physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition can be sterile.

IV. Methods of Determining Numbers of Cells Expressing a 4G7 Derived Anti-CD19 CAR The present disclosure provides a method to determine the number of cells present in a sample that are expressing an anti-CD19 CAR (e.g., a CAR comprising a 4G7-derived scFv such as UCART19 or ALLO-501) or a fragment thereof. For example, it can be desirable to determine the number of immune cells present in a sample obtained from a subject that are expressing an anti-CD19 CAR (e.g., a CAR comprising a 4G7-derived scFv such as UCART19 or ALLO-501 or ALLO-501A) or a fragment thereof. Or it can be desirable to determine the number of cells transfected and expressing an anti-CD19 CAR (e.g., a CAR comprising a 4G7-derived scFv such as UCART19 or ALLO-501 or ALLO-501A) or a fragment thereof, which can be used as a measure of the level of efficiency of the transfection. The disclosed method can be employed in these and other applications in which it is desirable to determine the number of cells present in a sample that are expressing a molecule of interest such as an anti-CD19 CAR (e.g., a CAR comprising a 4G7-derived scFv such as UCART19 or ALLO-501 or ALLO-501A) or a fragment thereof.

Thus, a method of determining a number of cells presenting a molecule in a sample wherein the molecule comprises a polypeptide comprising an anti-CD19 CAR (e.g., a CAR comprising a 4G7-derived scFv such as UCART19 or ALLO-501 or ALLO-501A) or a fragment thereof is provided.

In some embodiments, a sample comprising cells known or suspected to be expressing a molecule of interest comprising a polypeptide comprising an anti-CD19 CAR (e.g., a CAR comprising a 4G7-derived scFv such as UCART19 or ALLO-501 or ALLO-501A) or a fragment thereof is provided.

The sample is then contacted with an antigen binding molecule that specifically binds the molecule of interest, under conditions that permit the formation of a binding complex comprising a cell present in the sample and the antigen binding molecule. The antigen binding molecule can be an antigen binding molecule (or fragment thereof) disclosed herein, e.g., in the Figures, Sequence Listing or the instant section of the disclosure. Any antigen binding molecule that specifically binds a polypeptide comprising an anti-CD19 CAR (e.g., a CAR comprising a 4G7-derived scFv such as UCART19 or ALLO-501 or ALLO-501A) or a fragment thereof can be employed in the disclosed method. Multiple examples of suitable antigen binding molecules are provided herein, e.g., those having one or more of the CDRs shown in Tables 1c and 1d and described herein.

The cell can be of any type, and can be human or non-human (e.g., mouse, rat, rabbit, hamster, etc.). In some embodiments, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). In some embodiments, the immune cells are T cells including T cytotoxic, T helper and Treg cells. In specific embodiments, the cells are T cells, which can be obtained as described herein and by methods known in the art. Any type of immune cell can be employed in this embodiment of the disclosed method, and the cell can be a human or non-human cell (including both prokaryotic and eukaryotic cells). Exemplary cells include, but are not limited to, immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

In some embodiments, the sample comprising an anti-CD19 CAR (e.g., a CAR comprising a 4G7-derived scFv such as UCART19 or ALLO-501 or ALLO-501A) or a fragment thereof is contacted with an anti-Id antibody disclosed herein that specifically binds a 4G7 derived binding molecule. In some embodiments, the anti-Id antibody comprises a detectable label. In some embodiments, the detectable label conjugated anti-Id antibody is contacted with the sample expressing an anti-CD19 CAR (e.g., a CAR comprising a 4G7-derived scFv such as UCART19 or ALLO-501 or ALLO-501A), under conditions that permit the formation of a binding complex comprising a cell present in the sample and the anti-Id antibody. Any anti-Id antibody that specifically binds an anti-CD19 CAR (e.g., a CAR comprising a 4G7-derived scFv such as UCART19 or ALLO-501 or ALLO-501A) can be employed in the disclosed method. Multiple examples of suitable anti-Id antibody are provided herein, e.g., those having one or more of the CDRs shown in Table 1c or 1d.

Any detectable label can be employed in the methods, as described herein, and suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science). Suitable optical dyes, including fluoro-phores, are described in Johnson, *Molecular Probes Handbook: A Guide to Fluorescent Probes and Labeling Techniques*, 11th Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I), photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNA-BEADS), etc. Strategies for the labeling of proteins are well known in the art and can be employed in the disclosed method. See, e.g., Obermaier et al., (2015) *Methods MolBiol* 1295:153-65; Strack (2016) *Nature Methods* 13:33; *Site-Specific Protein Labeling: Methods and Protocols*, (Gautier and Hinner, eds.) 2015, Springer. In some embodiments, the detectable label is a phycoerythrin (PE) or allophycocyanin (APC) fluorescent probe.

The label can be associated with the anti-Id antibody at any position in the molecule, although it can be desirable to associate the label with the antibody at a position (or positions, if multiple labels are employed) at a point such that the binding properties of the molecule are not modified (unless such modified binding activity is desired). Any antigen binding molecule that specifically binds a 4G7 derived binding molecule (or fragment thereof) can be employed, such as those disclosed herein, e.g., those having one or more of the CDRs shown in Table 1c or 1d.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS®, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are desirable in the disclosed method.

The number of cells present in a binding complex in the sample is determined. The specific method employed to determine the number of cells present in a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The output of these detection methods can be in the form of a number of cells or the output can be of a form that allows the calculation of the number of cells based on the output.

V. Methods of Determining the Presence or Absence of a 4G7 Derived Anti-CD19 CAR In some embodiments, knowing whether a molecule comprising an anti-CD19 CAR (e.g., a CAR comprising a 4G7-derived scFv such as UCART19 or ALLO-501) or a fragment thereof, is present or absent from a sample is sufficient information. For example, it can be beneficial to know that such a molecule is being expressed, regardless of the level of expression. In other cases, it can be desirable to know if a purification process or step designed to remove such a molecule has been effective. Thus, the qualitative determination of the presence or absence of an anti-CD19 CAR (e.g., a CAR comprising a 4G7-derived scFv such as UCART19 or ALLO-501 or ALLO-501A) or a fragment thereof, can be useful in multiple applications.

In some embodiments, a method of determining the presence or absence in a sample of a polypeptide comprising an anti-CD19 CAR (e.g., a CAR comprising a 4G7-derived scFv such as UCART19 or ALLO-501 or ALLO-501A) or a fragment thereof, in a sample is provided.

In some embodiments, the method comprises providing a sample known or suspected to comprise a polypeptide comprising an anti-CD19 CAR (e.g., a CAR comprising a 4G7-derived scFv such as UCART19 or ALLO-501 or ALLO-501A) or a fragment thereof.

The disclosure provides an antigen binding molecule that specifically binds a polypeptide comprising an anti-CD19 CAR (e.g., a CAR comprising a 4G7-derived scFv such as UCART19 or ALLO-501 or ALLO-501A) or a fragment thereof, which includes a detectable label. Suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I). Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs, Inc., Genbank Accession Number U55762), blue fluorescent protein (BFP, Quantum Biotechnologies, Inc.; Stauber, (1998) *Biotechniques* 24:462-471; Heim et al., (1996) *Curr. Biol.* 6: 178-182), enhanced yellow fluorescent protein (Clontech Labs, Inc.), luciferase (Ichiki et al., (1993) *J. Immunol.* 150:5408-5417), magnetic labels (e.g., DYNABEADS®), etc. can also be employed. Strategies for the labeling of proteins are well known in the art and can be employed in the disclosed methods. The label can be associated with the antigen binding molecule at any position in the molecule, although it can be desirable to associate the label with the molecule at a position (or positions, if multiple labels are employed) at a point such that the binding properties of the molecule are not modified (unless such modified binding activity is desired). Any antigen binding molecule that specifically binds a polypeptide comprising an anti-CD19 CAR (e.g., a CAR comprising a 4G7-derived scFv such as UCART19 or ALLO-501 or ALLO-501A) or a fragment thereof can be employed, such as those disclosed herein, e.g., those having one or more of the CDRs described in Tables 1c and 1d.

Next, the sample is contacted with the antigen binding molecule under conditions that permit the formation of a binding complex comprising a cell present in the sample and the antigen binding molecule.

The sample is contacted with the antigen binding molecule, under conditions that permit the formation of a binding complex between a polypeptide comprising an anti-CD19 CAR (e.g., a CAR comprising a 4G7-derived scFv such as UCART19 or ALLO-501 or ALLO-501A) or a fragment thereof and the antigen binding molecule. Conditions that permit the formation of a binding complex will be dependent on a variety of factors. Since the component parts of a binding complex can be disposed on surfaces as described herein, formed binding complexes can also be disposed on surfaces.

At this stage, no binding complexes can have formed, or a plurality of binding complexes comprising one or more antigen binding molecules bound to a polypeptide comprising an anti-CD19 CAR (e.g., a CAR comprising a 4G7-derived scFv such as UCART19 or ALLO-501 or ALLO-501A) or a fragment thereof can have formed. Unbound molecules comprising an anti-CD19 CAR (e.g., a CAR comprising a 4G7-derived scFv such as UCART19 or ALLO-501 or ALLO-501A) or a fragment thereof and/or unbound antigen binding molecules can also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. In some embodiments, separation of the binding complex is not required for detection.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, should be avoided when performing this step of the method.

The presence or absence of a binding complex, which will comprise a polypeptide comprising an anti-CD19 CAR (e.g., a CAR comprising a 4G7-derived scFv such as UCART19 or ALLO-501 or ALLO-501A) or a fragment thereof and an antigen binding molecule, can be detected. The specific method employed to detect the presence or absence of a binding complex will typically be dependent on the nature of the label selected. In some embodiments, the detection method is by colorimetric assay. The result of the method is a qualitative assessment of the presence or absence of the antigen binding molecule comprising the detectable label, and thus, the presence or absence of its binding partner, a polypeptide comprising an anti-CD19 CAR (e.g., a CAR comprising a 4G7-derived scFv such as UCART19 or ALLO-501 or ALLO-501A) or a fragment thereof.

As is the case with the disclosed methods, the polypeptide comprising an anti-CD19 CAR (e.g., a CAR comprising a 4G7-derived scFv such as UCART19 or ALLO-501 or ALLO-501A) or a fragment thereof can be disposed in any environment. In some embodiments, the polypeptide comprising an anti-CD19 CAR (e.g., a CAR comprising a 4G7-derived scFv such as UCART19 or ALLO-501 or ALLO-501A) or a fragment thereof is expressed on the surface of a cell. In this embodiment, the cell can be of any type, and can be human or non-human (e.g., mouse, rat, rabbit, hamster, etc.). In some embodiments, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially suitable. In specific embodiments, the cells are T cells, which can be obtained as described herein and by methods known in the art. Any type of immune cell can be employed in this embodiment of the disclosed method, and the cell can be a human or non-human cell. Exemplary cells include, but are not limited to, immune cells such as T cells, tumor infiltrating lymphocytes (TILs), NK cells, dendritic cells, and NK-T cells. The T cells can be autologous, allogeneic, or heterologous. In additional embodiments, the cells are T cells presenting a TCR. The T cells can be CD4+ T cells or CD8+ T cells. When a T cell is employed in the disclosed methods, the T cell can be an in vivo T cell or an in vitro T cell. Further, cells can be derived from a stem cell, such as an iPSC cell, cord blood cell, or mesenchymal stem cell.

In some embodiments, the cell can be disposed in, or isolated from, any environment capable of maintaining the cell in a viable form, such as blood, tissue or any other sample obtained from a subject, cell culture media, tissue grown ex vivo, a suitable buffer, etc. In some embodiments, the cell is in a formalin-fixed sample. In some embodiments, the sample is a formalin-fixed paraffin embedded tissue (FFPE).

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control.

The foregoing written specification is considered to be sufficient to enable one skilled in the art to practice the disclosure. The foregoing description and Examples that follow detail certain embodiments of the disclosure and describe the best mode contemplated by the inventors. It will be appreciated, however, that no matter how detailed the foregoing can appear in text, the disclosure can be practiced in many ways and the disclosure should be construed in accordance with the appended claims and any equivalents thereof.

EXAMPLES

Example 1: Generation of Anti-Idiotypic Antibodies to Anti-Human CD19 Antibody Clone 4G7

Balb/c mice were immunized with a 4G7-human Fab-8× His fusion protein (E2153) ("8×His" disclosed as SEQ ID NO: 45). Hybridomas were generated, cloned, and the secreted antibodies were screened for binding specificity to 4G7. Six E2153 generated subclones (E2153.1C4.E2, E2153.1D9.B4, E2153.1G5.H5, E2153.2H8.A8, E2153.3B11.B7, E2153.4D7.E11) were purified for further analysis. Antibody clones were identified and selected based on their ability to specifically bind the 4G7-derived scFv of the UCART19 and ALLO-501 CARs.

Example 2: Kinetic Analysis of Anti-Idiotypic Antibodies to Anti-Human CD19 Antibody Clone 4G7

Anti-m4G7 purified sub-clone antibodies were tested for binding to m4G7-hFab. Blocking effect was determined using a sandwich assay and binding confirmation to m4G7-scFv-Fc was determined using a Biacore assay at 25° C. Five of the purified anti-Ids sub-clones from Fusion E2153 demonstrate bind to m4G7-hFab. Sensor chip CAP (CAPture chip) #505 was used as a surface. After rehydrating the sensor chip CAP with water at 42° C. for 1 hour, the chip was dried with compressed air. The surface of the chip was conditioned using triplicate 1 min injections of regeneration solution at 10 µl/min. The regeneration solution included 3 parts of Regeneration Stock 1 (8 M guanidine-HCl) with 1 part Regeneration Stock 2 (1 M NaOH). Capture of Biotin CAPture reagent for 5 min at 2 µl/min was followed by capture of biotinylated Fusion E2153 anti-m4G7 purified sub-clones antibodies and control antibodies at 10 µg/ml for 1 min at 10 µl/min. As shown in FIG. 1, all biotinylated anti-Ids sub-clones captured well to the CAPture chip.

Blocking was performed with 20 µM amine-PEO-biotin for 1 min at 10 µl/min. Surfaces were regenerated with regeneration solution (mixture of 3 parts of Regeneration Stock 1 (8 M guanidine-HCl) with 1 part of Regeneration Stock 2 (1 M NaOH)) for 2 min at 10 µL/min. The 6 purified anti-Ids subclones from Fusion E2153 Balb/c mouse immunized with m4G7-hFab included E2153.1C4.E2 (0.51 mg/mL), E2153.1D9.B4 (0.41 mg/mL), E2153.1G5.H5 (0.37 mg/mL), E2153.2H8.A8 (0.45 mg/mL), E2153.3B11.B7 (0.49 mg/mL), and E2153.4D7.E11 (0.35 mg/mL).

Figure 2A:
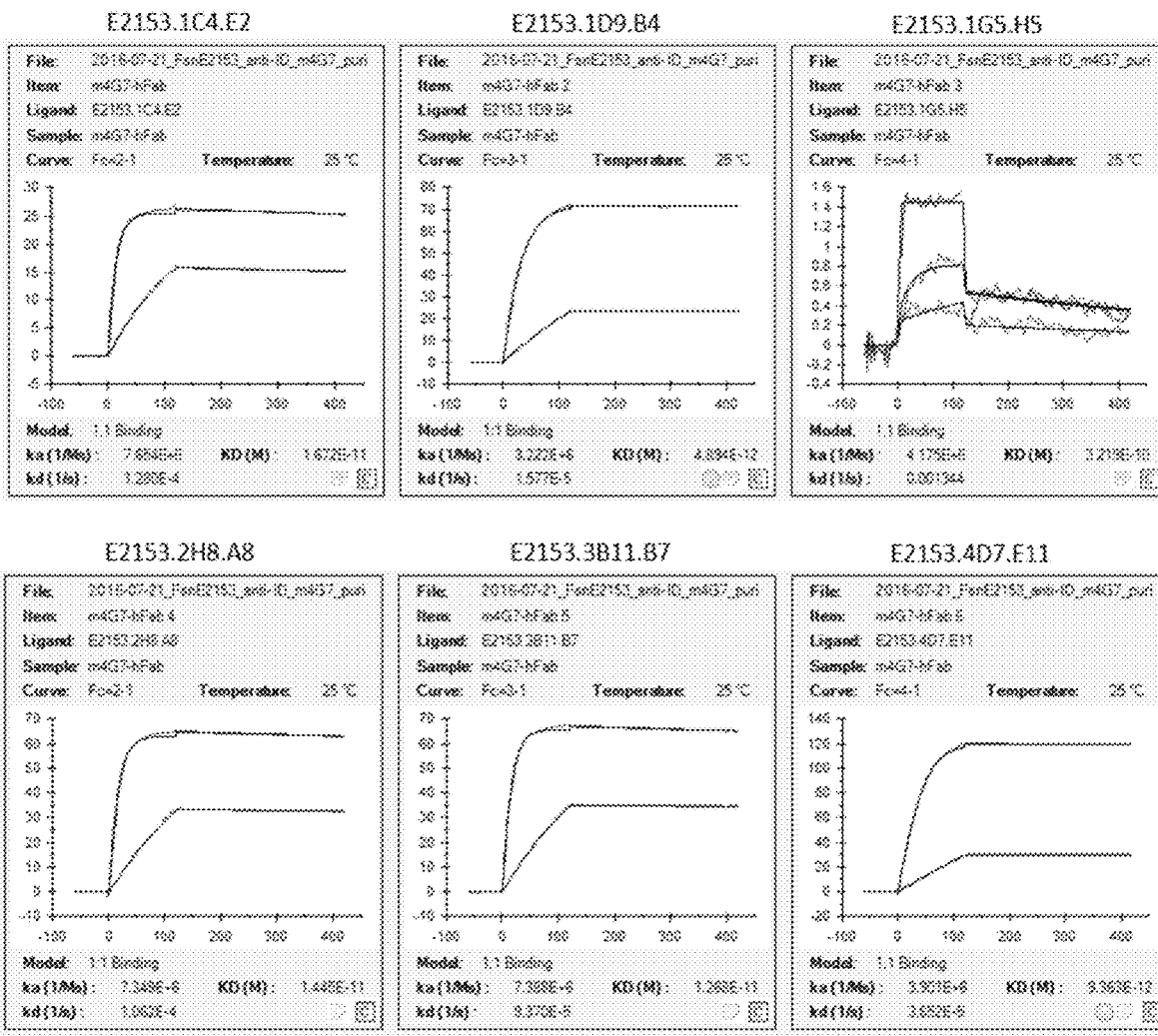
FIGS. 2A and 2B show kinetic fit plots for m4G7-hFab binding to the purified anti-Id antibody sub-clones generated from 4G7 fusion protein E2153 (FIG. 2A) and m4G7-hFab binding to negative control (FIG. 2B) at 25° C.
Figure 2B:
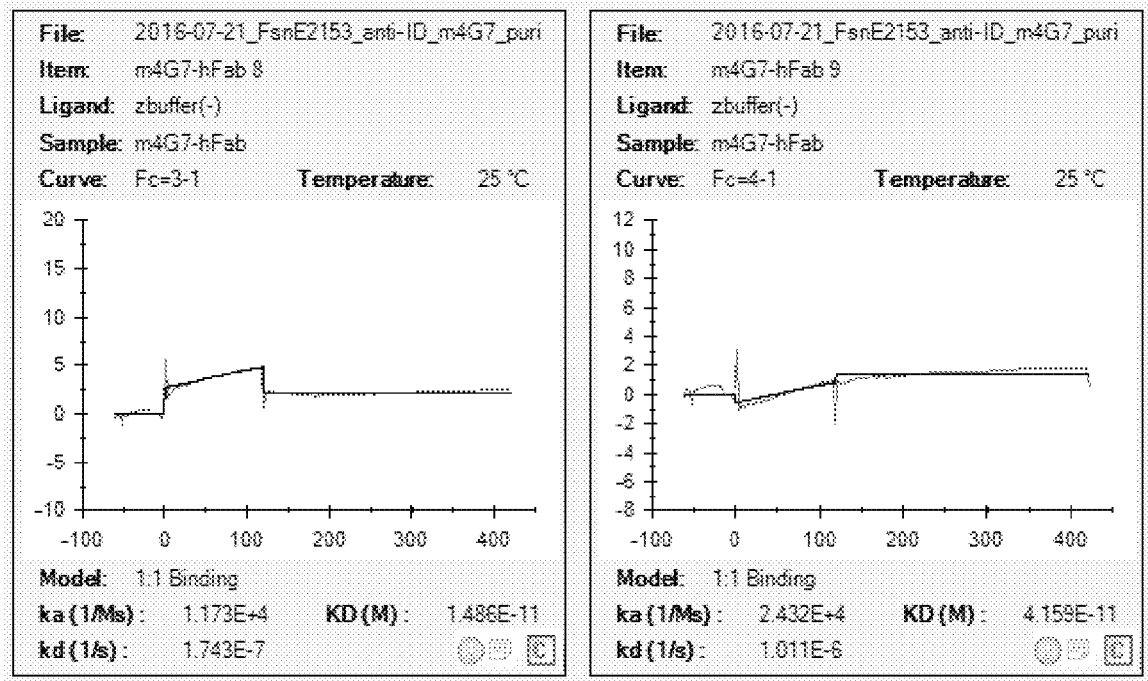

The following reagents were also used for the kinetic analysis at the indicated concentrations:

m4G7-hFab: m4G7 hFab 8×His, 0.92 mg/ml ("8×His" disclosed as SEQ ID NO: 45)
m4G7-scFv-Fc: 0.8 mg/ml, assumed M.W. 52 kDa
hCD19: hCD19-HIS-AVI 33.386 kDa assumed to be 18.4% active by CFCA (0.736 µM active concentration)
Framework ctrl: Framework match control for m4G7—Fab, 0.82 mg/ml
a-hKappa: control: biotinylated mouse anti-human kappa IgG1—monoclonal, Southern Biotech, 0.5 mg/ml
a-His: control: biotinylated mouse anti-His antibody control. R&D systems Cat. No. MAB050B For the kinetics assay, the buffer and m4G7-hFab at 1 nM, 10 nM, and 100 nM were injected for 2 min at 30 µL/min followed by 5 min dissociation. A summary of the binding kinetics is shown in Table 3. Kinetic fits for m4G7-hFab binding to 6 purified anti-Ids sub-clones from Fusion E2153 at 25° C. are shown in FIG. 2A. Kinetic fits for m4G7-hFab binding to negative control buffer at 25° C. are shown in FIG. 2B.

TABLE 3

Kinetics m4G7-hFab binding to 6 purified anti-Ids sub-clones from Fusion E2153

| Sample ID | $k_a$ (1/Ms) | $k_d$ (1/s) | $t_{1/2}$ (min) | $K_d$ (pM) |
|---|---|---|---|---|
| E2153.1C4.E2 | $7.65 \times 10^6$ | $1.28 \times 10^{-4}$ | 90 | 16.7 |
| E2153.3B11.B7 | $7.39 \times 10^6$ | $9.37 \times 10^{-5}$ | 123 | 12.7 |
| E2153.2H8.A8 | $7.35 \times 10^6$ | $1.06 \times 10^{-4}$ | 109 | 14.4 |
| E2153.4D7.E11 | very high affinity; outside instrument limits; heterogeneous at top concentration | | | |
| E2153.1D9.B4 | very high affinity; outside instrument limits; heterogeneous at top concentration | | | |
| E2153.1G5.H5 | no binding | | | |

For binding check to the framework match control for m4G7-hFab and m4G7-scFv-Fc, Buffer, framework match control for m4G7-hFab at 100 nM, m4G7-scFv-Fc at 100 nM, and m4G7-hFab at 100 nM were injected for 2 min at 30 µL/min followed by 5 min dissociation. The six purified anti-Ids sub-clones from Fusion E2153 did not bind to the framework match control for m4G7-hFab. In addition, all anti-Ids sub-clones with the exception of E2153.1G5.H5 bind to m4G7-scFv-Fc. Table 4, summarizes binding determinations for the framework match control for m4G7-hFab and m4G7-scFv-Fc to the purified anti-Ids sub-clones from Fusion E2153 at 25° C.

TABLE 4

Binding of anti-idiotypic antibodies to framework match control for m4G7-hFab and m4G7-scFv-Fc

| SampleID (biotinylated) | Captured to CAP surface | Binds to Framework control | Binds to m4G7-hFab | Binds to m4G7-scFv-Fc |
|---|---|---|---|---|
| E2153.4D7.E11 | Y | N | Y | Y |
| E2153.3B11.B7 | Y | N | Y | Y |
| E2153.2H8.A8 | Y | N | Y | Y |
| E2153.1G5.H5 | Y | N | N | N |
| E2153.1D9.B4 | Y | N | Y | Y |
| E2153.1C4.E2 | Y | N | Y | Y |
| a-His control | Y | Y | Y | N |

The blocking effect of m4G7-hFab binding to hCD19 by the purified anti-Ids sub-clones from Fusion E2153 was determined by the sandwich assay at 25° C. Sample 1 was injected for 2 min at 30 µL/min followed by 10 sec in buffer then Sample 2 was injected for 2 min at 30 µL/min followed by 3 min dissociation:

| Sample 1 | Sample 2 |
|---|---|
| buffer | buffer |
| buffer | hCD19 (300 nM) |
| m4G7-hFab (100 nM) | buffer |
| m4G7-hFab (100 nM) | hCD19 (300 nM) |

As shown in Table 5, no hCD19 sandwiches were observed with any of the m4G7 anti-Ids purified sub-clones. This data suggests that the anti-Id sub-clones do not bind hCD19.

TABLE 5

Blocking Effect of m4G7-hFab binding to hCD19 by to 6 purified anti-Ids sub-clones

| SampleID | Binds To m4G7-hFab | Sandwiches With hCD19 |
|---|---|---|
| E2153.4D7.E11 | yes | no |
| E2153.3B11.B7 | yes | no |
| E2153.2H8.A8 | yes | no |
| E2153.1G5.H5 | no | no |
| E2153.1D9.B4 | yes | no |
| E2153.1C4.E2 | yes | no |
| Ms a-human Kappa (+) control | yes | yes |

Example 3: Comparison of Anti-UCART19 Antibodies

Figure 3A:
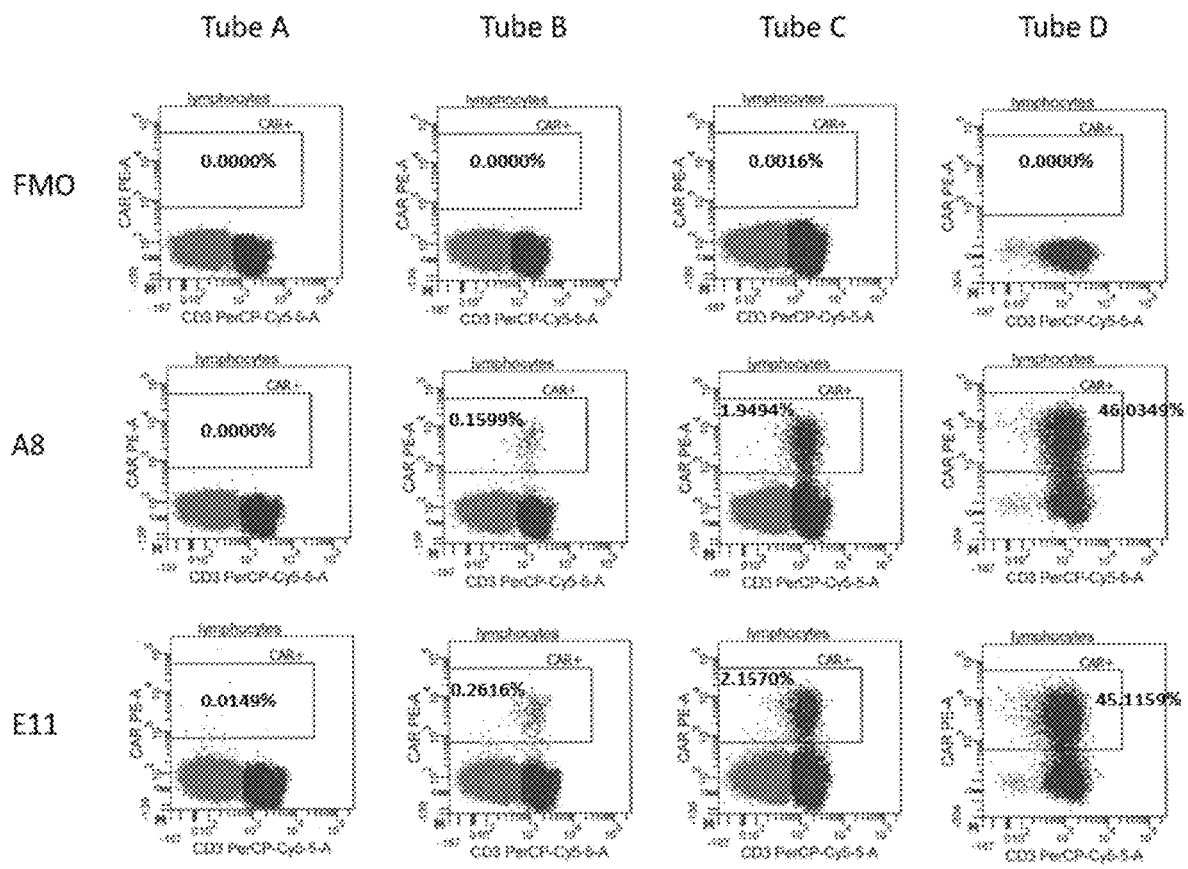
FIGS. 3A and 3B show exemplary flow cytometry plots of comparing commercially available anti mouse F(ab')2 antibody and anti-Id antibody clones A8 and Eli for binding to UCART19 cells. Tube A included blood from a healthy volunteer; Tube B: blood from healthy volunteer+100,000 UCART19 transduced cells per mL; Tube C: blood from healthy volunteer+1 million UCART19 transduced cells per mL and Tube D: 10 million UCART19 transduced cells per mL.
Figure 3B:
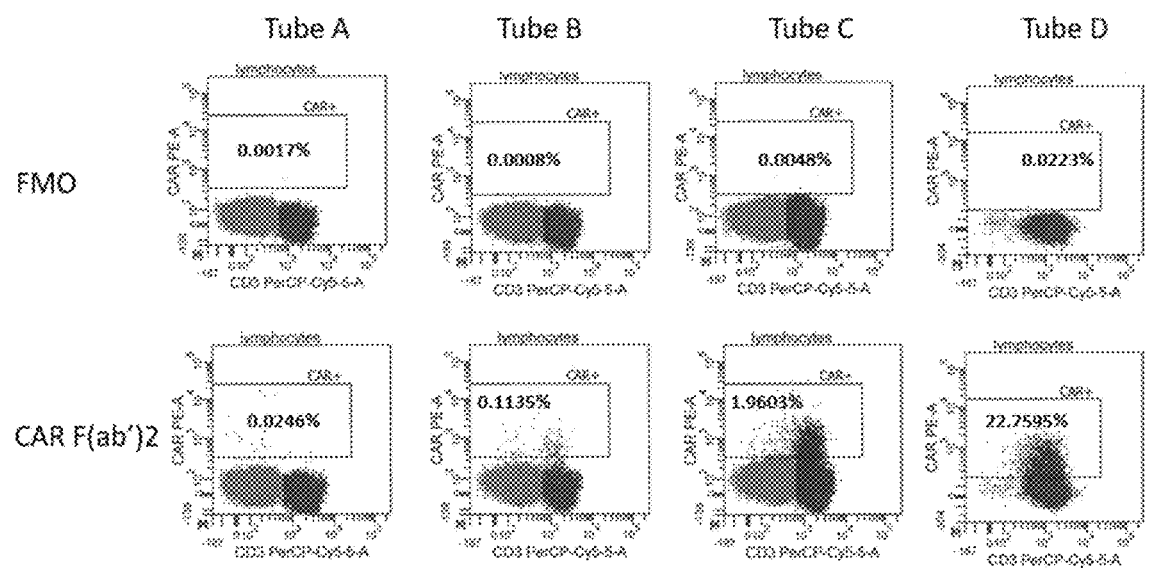

Commercially available anti mouse F(ab')2 antibody from Jackson Immunoresearch and antibodies A8 and E11 antibodies described in Examples 1 and 2, were tested at four UCART19 concentrations (blank, 100,000 cells per mL in blood, 1 million cells per mL in blood and 10 million cells per mL in PBS). Exemplary flow cytometry plots are shown in FIGS. 3A and 3B. Tube A included blood from a healthy volunteer; Tube B: blood from healthy volunteer+100,000 UCART19 transduced cells per mL; Tube C: blood from healthy volunteer+1 million UCART19 transduced cells per mL and Tube D: 10 million UCART19 transduced cells per mL.

The A8 antibody detects the UCART19 positive cells in the absence of aspecific binding. The E11 antibody shows slight aspecific binding. The A8 and E11 antibodies give a strong PE positive signal allowing clear discrimination between UCART19 positive and negative cells. A ten-fold increase in % CAR+ cells is seen between tube B and C both for detection with the A8 and E11 antibody. For tube D, a 20-fold increase is seen rather than the expected 10-fold increase.

Example 4: Blocking UCART19

Figure 4A:
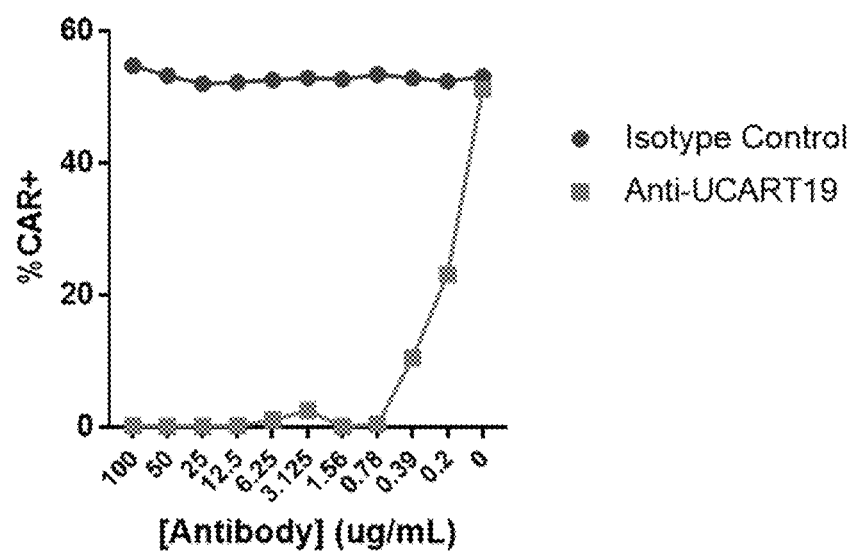
FIGS. 4A-4E show exemplary results of blocking experiments using anti-Id antibody A8 labeled anti-UCART19.
Figure 4B:
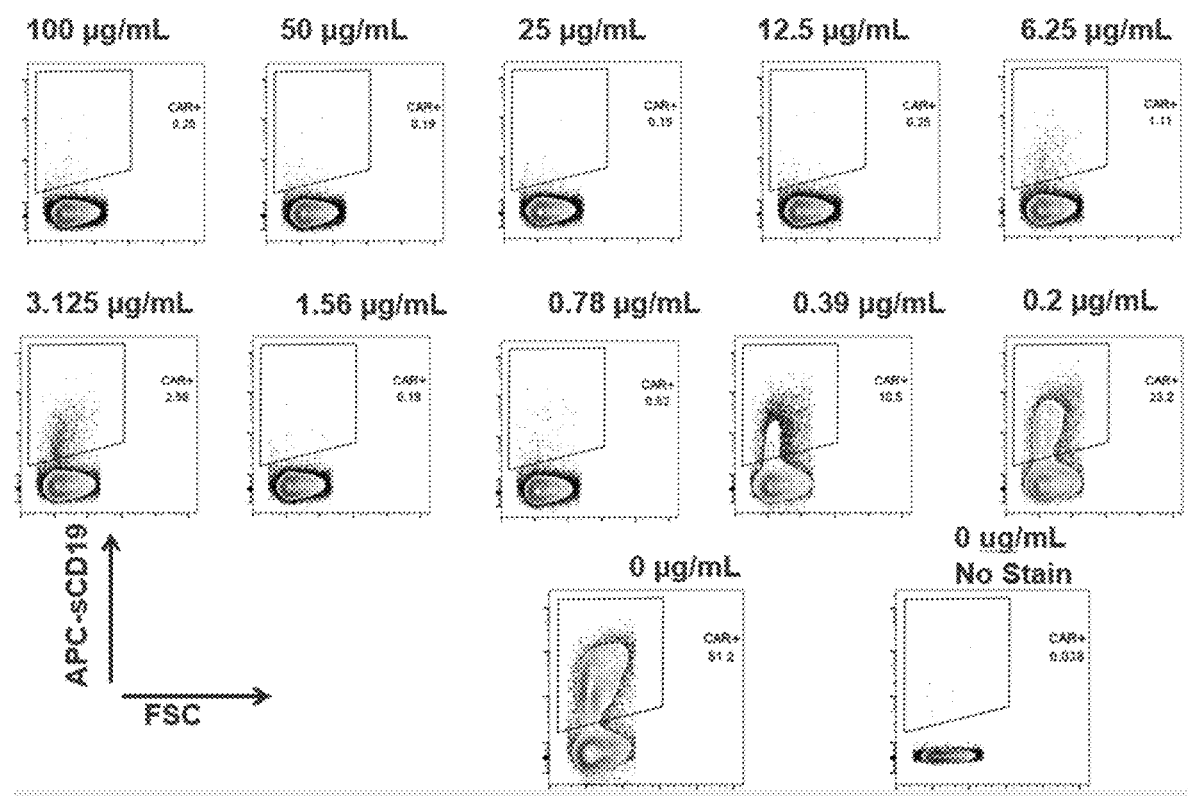
Figure 4C:
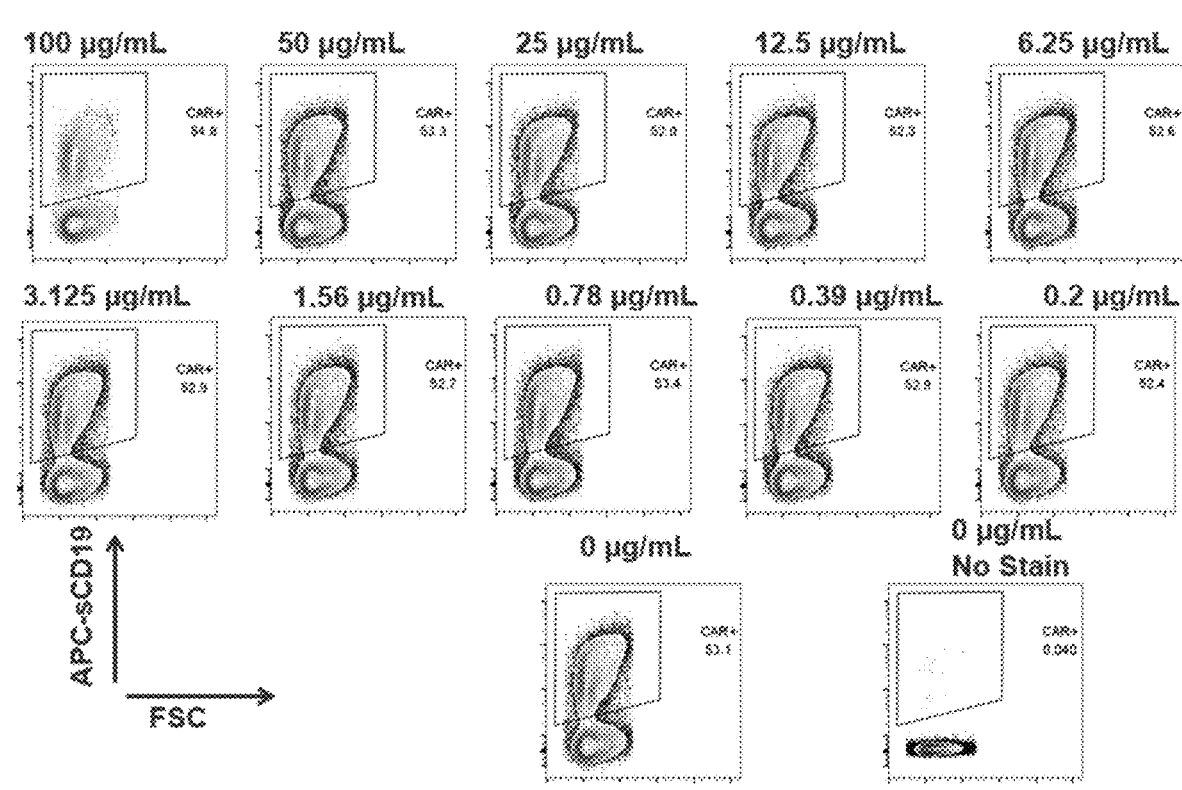

Fresh UCART19 cells were stained with serial dilutions of unconjugated anti-UCART19 idiotype antibody A8 (E2153.2H8.A8), and unconjugated mouse IgG1 Isotype control. Cells were incubated at 4° C. for 20 min followed by a wash with BD FACS stain buffer. Secondary staining was performed with AF647-conjugated soluble CD19-hFc for 20 min at 4° C. Cells were washed with BD FACS stain buffer followed by flow cytometry. As shown in FIGS. 4A-4C, anti-UCART19 antibody blocks APC-sCD19 binding. FIGS. 4B and 4C show flow cytometry plots of increasing concentration of idiotype Ab A8 (E2153.2H8.A8) (FIG. 4B) and unconjugated mouse IgG1 Isotype control (FIG. 4C).

Figure 4D:
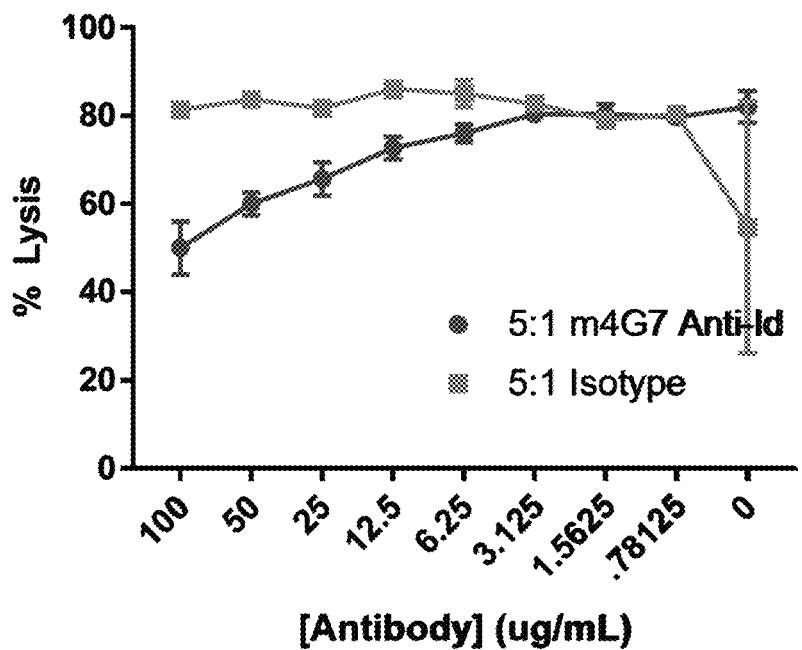
Figure 4E:
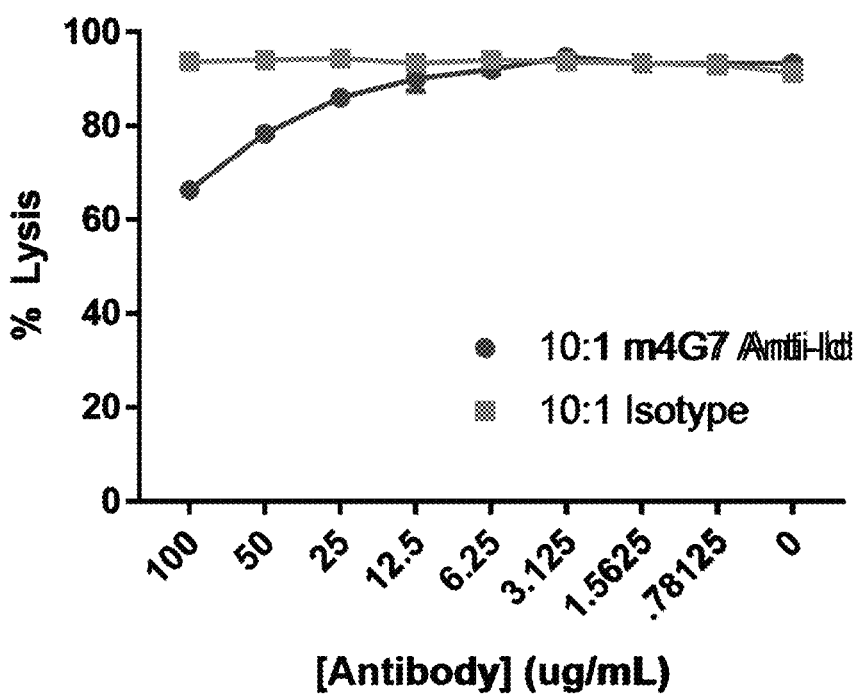

Blocking of UCART19 cells with anti-idiotype antibody A8 was also assessed on thawed UCART19 cells. Target Raji-Luc-GFP cells were plated at 5000 cells/well in 50 uL. UCART19 cells were thawed and allowed to recover at 37° C. for 1 hour. After recovery, UCART19 concentration was adjusted to 5:1 and 10:1 effector:target ratios (E:T) using Day 13 CAR % data. UCART19 cells were incubated at 37° C. for 30 minutes using various concentrations of antibody (m4G7 anti-Id and IgG1 Isotype). Each ratio was plated in triplicates on the Raji-Luc-GFP. The cell mixture was incubated at 37° C. for about 24 hours. 100 μL of Promega Bright Glo reagent was added to each well, mixed, incubated at room temperature for 3 minutes and then read on a luminometer. Target cells were normalized to be 0% lysed and % lysed was computed using the target alone cells. FIGS. 4D and 4E show blocking ability of anti-Id m4G7 (A8) at 5:1 and 10:1 E:T ratios, respectively.

Figure 5A:
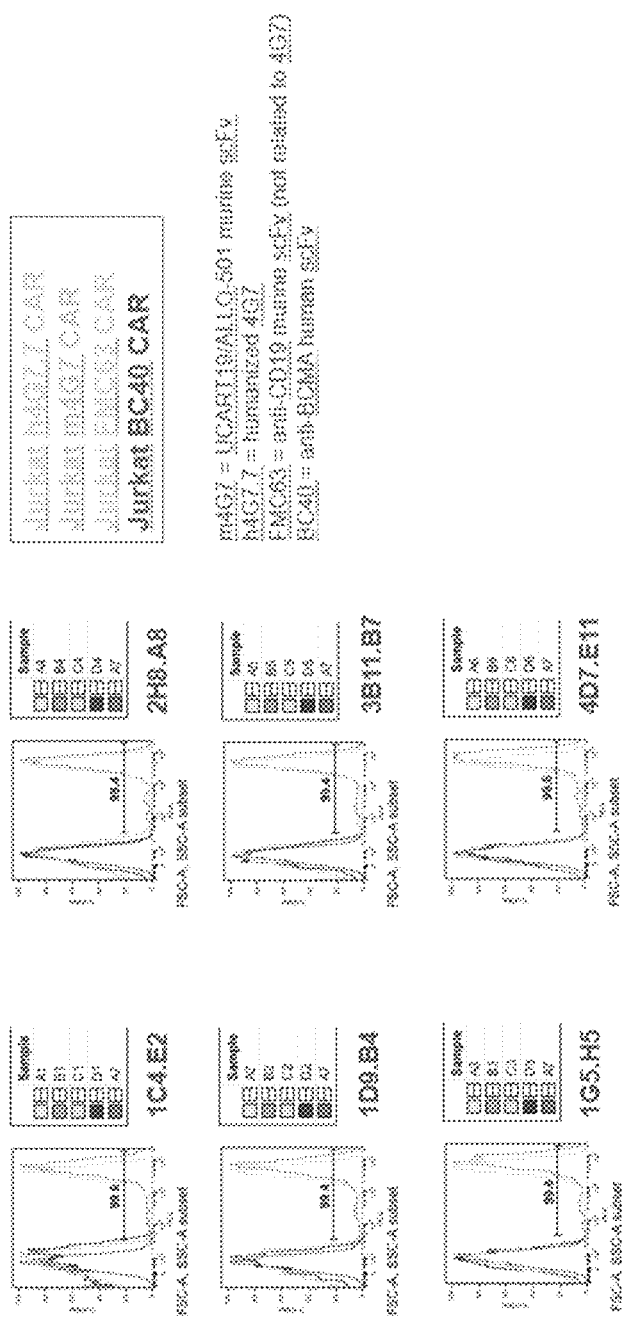
FIG. 5A shows exemplary flow cytometry plots of anti-idiotype antibody experiments to determine binding to Jurkat cells expressing CARs with an scFv derived from murine 4G7 (m4G7), a humanized 4G7 (h4G7.7), FMC63 anti-CD19 murine scFv (not related to 4G7) or BC40, an anti-BCMA human scFv.
Figure 5B:
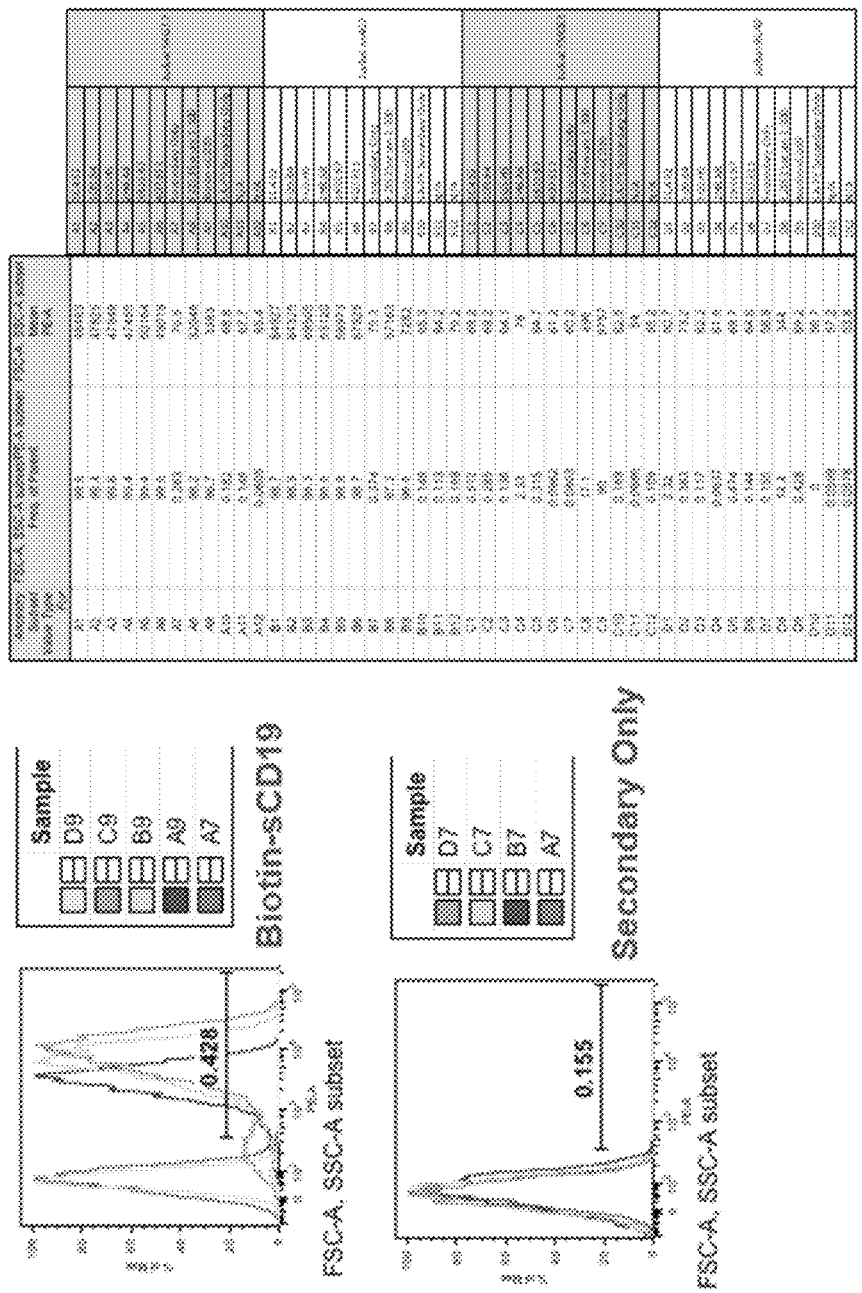
FIG. 5B shows flow cytometry plots of a positive control using sCD19-Fc binding to all anti-CD19 CARs expressed on Jurkat cells.

Example 5: Binding of Anti-Idiotype Antibodies to 4G7 Derived Chimeric Antigen Receptors This example demonstrates specific binding of anti-idiotype antibodies to CARs to both human h4G7.7 and murine m4G7 CARs. As shown in FIG. 5A, anti-idiotype antibodies described herein bind to Jurkat cells expressing CARs with an scFv derived from murine 4G7 (m4G7) and humanized 4G7 (h4G7.7). Anti-idiotype antibodies of the present disclosure do not bind to CARs with an FMC63 anti-CD19 murine scFv (not related to 4G7) or BC40, an anti-BCMA human scFv. sCD19-Fc binding to all anti-CD19 CARs expressed on Jurkat cells was used as a positive control (FIG. 5B).

Figure 6A:
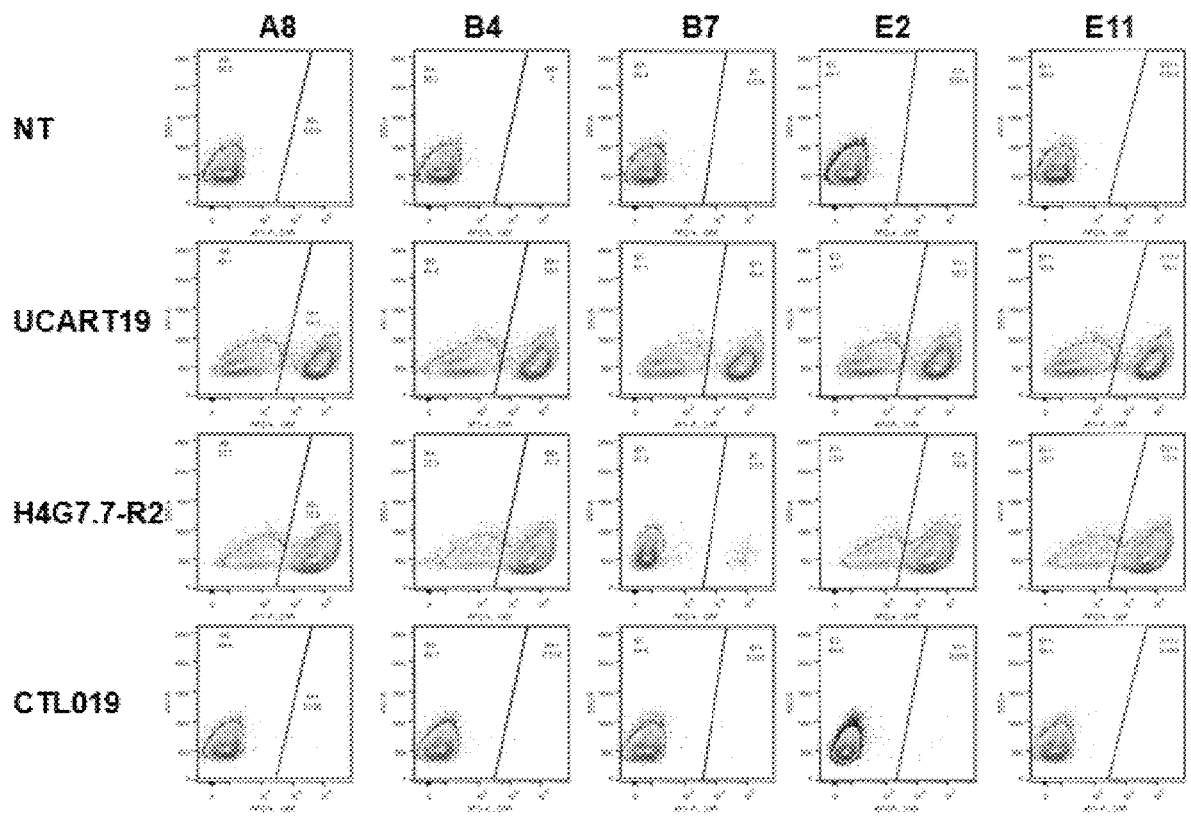
FIG. 6A and FIG. 6B show exemplary flow cytometry plots of anti-idiotype antibodies binding to h4G7.7 and UCART19 expressed on primary human T cells but do not bind to an FMC63-derived CAR (CTL-019) (FIG. 6A). sCD19-Fc was used as a positive control demonstrating binding to all anti-CD19 CARs expressed on primary human T cells (FIG. 6B).
Figure 6B:
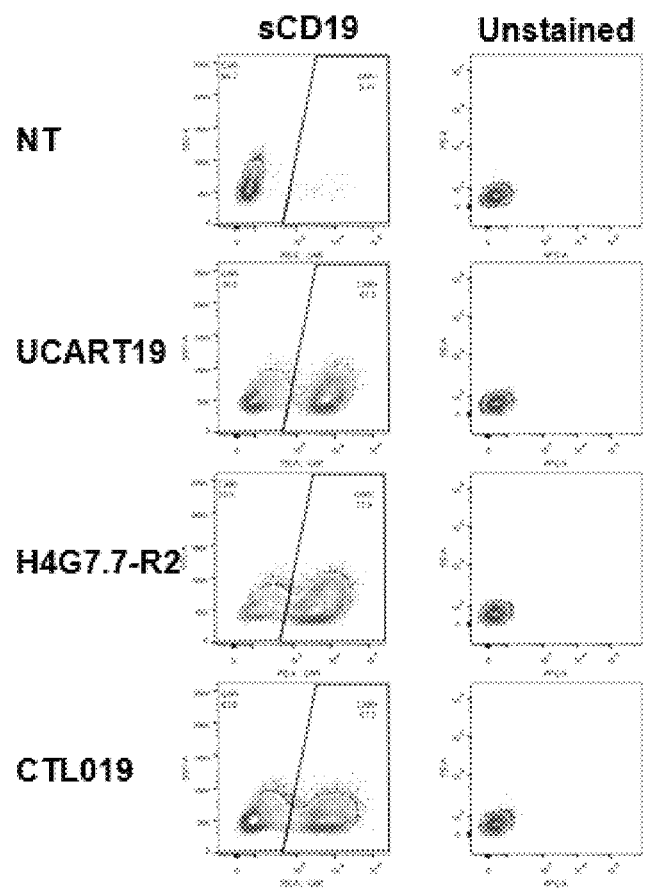

Binding of anti-idiotype antibodies to anti-CD19 CARs expressed on primary human T cells. Anti-idiotype antibodies show specific binding to both h4G7.7 and UCART19 expressed on primary human T cells but do not bind to an FMC63-derived CAR (CTL-019) (FIG. 6A). sCD19-Fc binding to all anti-CD19 CARs expressed on primary human T cells was used as a positive control (FIG. 6B).

Figure 7:
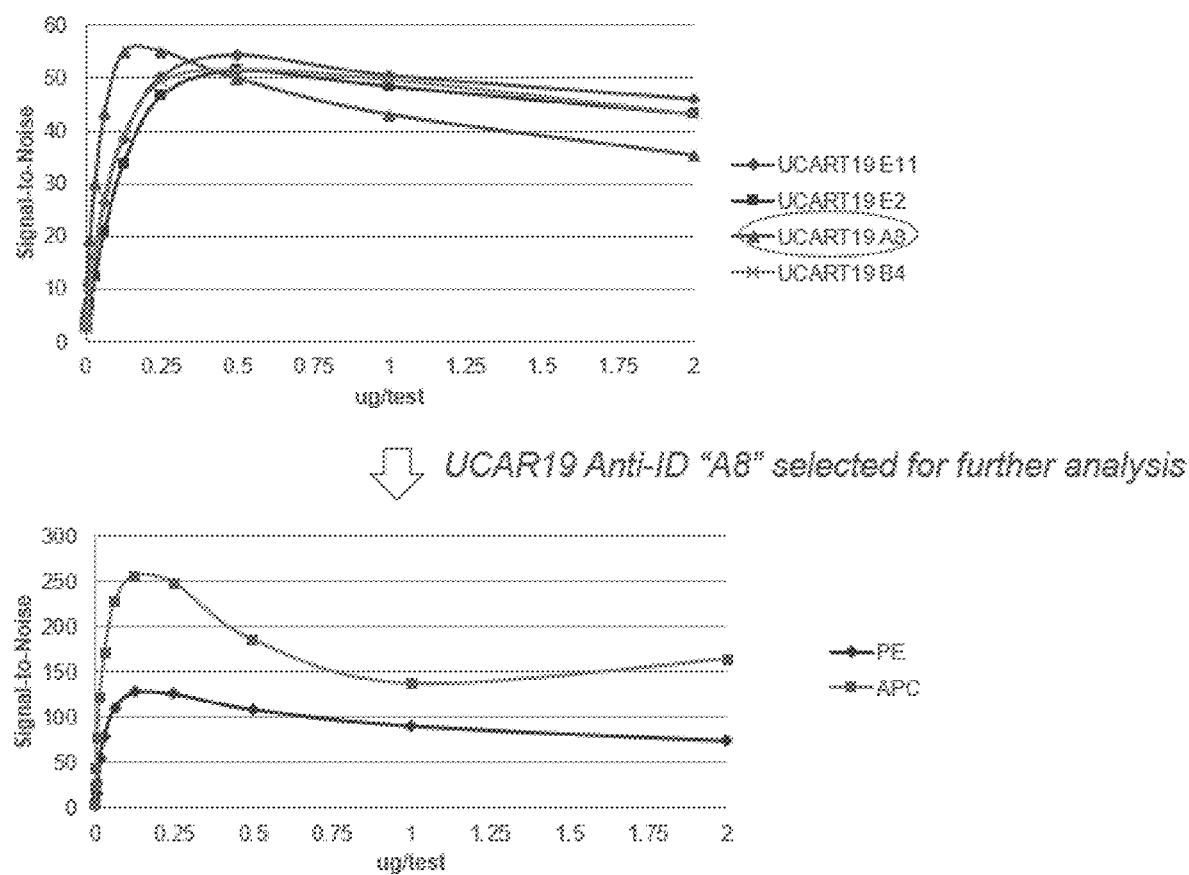
FIG. 7 shows signal-to-noise ratios of anti-Id clones E11, E2, A8, and B4 at increasing concentrations.
Figure 8:
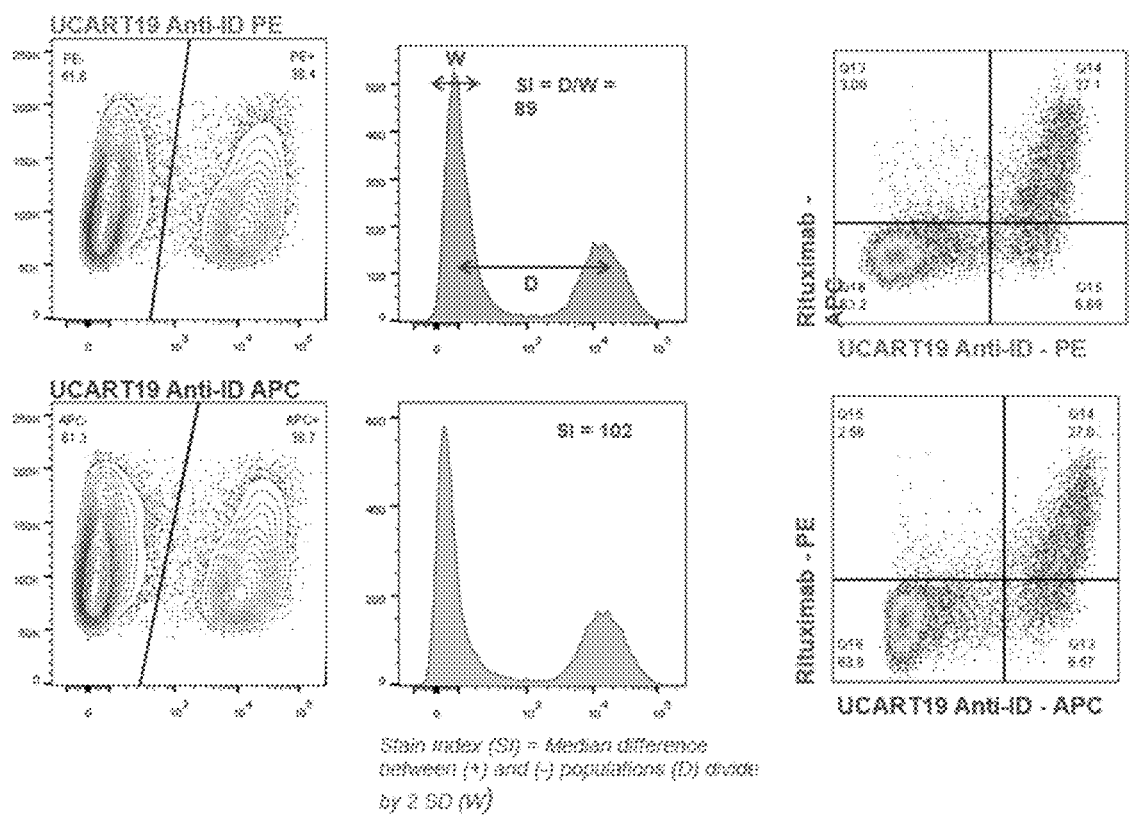
FIG. 8 shows stain index and flow cytometry plots of anti-idiotype antibody A8 conjugated to phycoerythrin (PE) or allophycocyanin (APC) fluorescent probes.

Example 6: Conjugating Fluorescent Probes for FACS Analysis to Anti-Idiotype Antibodies As shown in FIG. 7, clone A8 demonstrated a better signal-to-noise ratio at lower test volume than the other anti-idiotype antibodies. Anti-idiotype antibodies were conjugated to phycoerythrin (PE) or allophycocyanin (APC) fluorescent probes for use as a FACS analysis reagent. Both APC conjugation and PE conjugated A8 detected UCART19, however APC-conjugated clone A8 gave a stain index of 102 and PE conjugated A8 gave a stain index of 82 (FIG. 8). When conjugated to a bright fluorochrome (e.g., PE or APC), A8 stains UCART19 or ALLO-501 cells with a high MFI and low background.

What is claimed is:

1. An isolated antibody that specifically binds a molecule comprising an anti-CD19 scFv comprising the amino acid sequence of SEQ ID NO:36, wherein the antibody comprises
   (a) a heavy chain variable region (VH) CDR1 comprising the amino acid sequence of SEQ ID NO: 15 or 21, a VH CDR2 comprising the amino acid sequence of SEQ ID NO: 16 or 22, a VH CDR3 comprising the amino acid sequence of SEQ ID NO: 17 or 23, a light chain variable region (VL) CDR1 comprising the amino acid sequence of SEQ ID NO: 18, a VL CDR2 comprising the amino acid sequence of SEQ ID NO: 19, and a VL CDR3 comprising the amino acid sequence of SEQ ID NO: 20;
   (b) a VH CDR1 comprising the amino acid sequence of SEQ ID NO: 24 or 29, a VH CDR2 comprising the amino acid sequence of SEQ ID NO: 25 or 30, a VH CDR3 comprising the amino acid sequence of SEQ ID NO: 26, a VL CDR1 comprising the amino acid sequence of SEQ ID NO: 27, a VL CDR2 comprising the amino acid sequence of SEQ ID NO: 19, and a VL CDR3 comprising the amino acid sequence of SEQ ID NO: 28; or
   (c) a VH CDR1 comprising the amino acid sequence of SEQ ID NO: 24 or 29, a VH CDR2 comprising the amino acid sequence of SEQ ID NO: 31 or 33, a VH CDR3 comprising the amino acid sequence of SEQ ID NO: 26, a VL CDR1 comprising the amino acid sequence of SEQ ID NO: 27, a VL CDR2 comprising the amino acid sequence of SEQ ID NO: 19, and a VL CDR3 comprising the amino acid sequence of SEQ ID NO: 32.

2. The isolated antibody of claim 1 comprising a VH amino acid sequence that is at least about 95%, at least about 96%, at least about 97%, at least about 98%, or at least about 99% identical to the amino acid sequence of SEQ ID NO: 1, 2 or 3.

3. The isolated antibody of claim 1, comprising a VL amino acid sequence that is at least about 95%, at least about 96%, at least about 97%, at least about 98%, at least about 99%, or about 100% identical to a VL comprising the amino acid sequence of SEQ ID NO: 7, 8, 9, or 10.

4. The isolated antibody of claim 1, comprising
   (a) a VH CDR1 comprising the amino acid sequence of SEQ ID NO:21;
   (b) a VH CDR2 comprising the amino acid sequence of SEQ ID NO: 22;
   (c) a VH CDR3 comprising the amino acid sequence of SEQ ID NO: 23;
   (d) a VL CDR1 comprising the amino acid sequence of SEQ ID NO: 18;
   (e) a VL CDR2 comprising the amino acid sequence of SEQ ID NO: 19; and
   (f) a VL CDR3 comprising the amino acid sequence of SEQ ID NO: 20.

5. The isolated antibody of claim 4, comprising
   (a) a VH comprising the amino acid sequence of SEQ ID NO:1; and
   (b) a VL comprising the amino acid sequence of SEQ ID NO: 7.

6. The isolated antibody of claim 4, comprising
   (a) a VH comprising the amino acid sequence of SEQ ID NO: 1; and
   (b) a VL comprising the amino acid sequence of SEQ ID NO: 10.

7. The isolated antibody of claim 1, comprising
   (a) a VH CDR1 comprising the amino acid sequence of SEQ ID NO: 29;
   (b) a VH CDR2 comprising the amino acid sequence of SEQ ID NO: 30;

(c) a VH CDR3 comprising the amino acid sequence of SEQ ID NO: 26;
(d) a VL CDR1 comprising the amino acid sequence of SEQ ID NO: 27;
(e) a VL CDR2 comprising the amino acid sequence of SEQ ID NO: 19; and
(f) a VL CDR3 comprising the amino acid sequence of SEQ ID NO: 28.

8. The isolated antibody of claim 7, comprising
(a) a VH comprising the amino acid sequence of SEQ ID NO: 2; and
(b) a VL comprising the amino acid sequence of SEQ ID NO: 8.

9. The isolated antibody of claim 1, comprising
(a) a VH CDR1 comprising the amino acid sequence of SEQ ID NO: 29;
(b) a VH CDR2 comprising the amino acid sequence of SEQ ID NO: 33;
(c) a VH CDR3 comprising the amino acid sequence of SEQ ID NO: 26;
(d) a VL CDR1 comprising the amino acid sequence of SEQ ID NO: 27;
(e) a VL CDR2 comprising the amino acid sequence of SEQ ID NO: 19; and
(f) a VL CDR3 comprising the amino acid sequence of SEQ ID NO: 32.

10. The isolated antibody of claim 9, comprising
(a) a VH comprising the amino acid sequence of SEQ ID NO: 3; and
(b) a VL comprising the amino acid sequence of SEQ ID NO: 9.

11. The isolated antibody of claim 1, wherein the isolated antibody further comprises a detectable label.

12. The isolated antibody of claim 11, wherein the detectable label is selected from the group consisting of a fluorescent label, a photochromic compound, a proteinaceous fluorescent label, a magnetic label, a radiolabel, and a hapten.

13. A polynucleotide encoding the isolated antibody of claim 1.

14. A vector comprising the polynucleotide of claim 13.

15. A cell comprising the polynucleotide of claim 13.

16. A method of making an isolated antibody that specifically binds a molecule comprising an anti-CD19 scFv comprising the amino acid sequence of SEQ ID NO:36, the method comprising incubating the cell of claim 15 under suitable conditions.

17. An isolated antibody that specifically binds a molecule comprising an anti-CD19 scFv comprising the amino acid sequence of SEQ ID NO:36, wherein the antibody comprises
(a) a VH comprising the amino acid sequence of SEQ ID NO:1 and a VL comprising the amino acid sequence of SEQ ID NO: 7;
(b) a VH comprising the amino acid sequence of SEQ ID NO: 2 and a VL comprising the amino acid sequence of SEQ ID NO: 8;
(c) a VH comprising the amino acid sequence of SEQ ID NO: 3 and a VL comprising the amino acid sequence of SEQ ID NO: 9; or
(d) a VH comprising the amino acid sequence of SEQ ID NO: 1 and a VL comprising the amino acid sequence of SEQ ID NO: 10.

18. The isolated antibody of claim 17, comprising
(a) a VH CDR1 comprising the amino acid sequence of SEQ ID NO:15 or 21;
(b) a VH CDR2 comprising the amino acid sequence of SEQ ID NO: 16 or 22;
(c) a VH CDR3 comprising the amino acid sequence of SEQ ID NO: 17 or 23;
(d) a VL CDR1 comprising the amino acid sequence of SEQ ID NO: 18;
(e) a VL CDR2 comprising the amino acid sequence of SEQ ID NO: 19; and
(f) a VL CDR3 comprising the amino acid sequence of SEQ ID NO: 20.

19. The isolated antibody of claim 17, comprising
(a) a VH CDR1 comprising the amino acid sequence of SEQ ID NO: 24 or 29;
(b) a VH CDR2 comprising the amino acid sequence of SEQ ID NO: 25 or 30;
(c) a VH CDR3 comprising the amino acid sequence of SEQ ID NO: 26;
(d) a VL CDR1 comprising the amino acid sequence of SEQ ID NO: 27;
(e) a VL CDR2 comprising the amino acid sequence of SEQ ID NO: 19; and
(f) a VL CDR3 comprising the amino acid sequence of SEQ ID NO: 28.

20. The isolated antibody of claim 17, comprising
(a) a VH CDR1 comprising the amino acid sequence of SEQ ID NO: 24 or 29;
(b) a VH CDR2 comprising the amino acid sequence of SEQ ID NO: 31 or 33;
(c) a VH CDR3 comprising the amino acid sequence of SEQ ID NO: 26;
(d) a VL CDR1 comprising the amino acid sequence of SEQ ID NO: 27;
(e) a VL CDR2 comprising the amino acid sequence of SEQ ID NO: 19; and
(f) a VL CDR3 comprising the amino acid sequence of SEQ ID NO: 32.

21. A method of determining a number of cells expressing an anti-CD19 scFv comprising the amino acid sequence of SEQ ID NO:36, the method comprising contacting a sample of cells with the isolated antibody of claim 1 and determining the number of cells expressing the anti-CD19 scFv in the sample.

22. The method of claim 21, wherein the anti-CD19 scFv is a component of a chimeric antigen receptor (CAR).

23. The method of claim 22, wherein the cells are CAR T cells.

24. A method of determining a number of cells presenting a polypeptide comprising an anti-CD19 scFv comprising the amino acid sequence of SEQ ID NO:36, wherein the method comprises:
(a) providing a sample comprising cells known or suspected to be presenting a polypeptide comprising an anti-CD19 scFv comprising the amino acid sequence of SEQ ID NO:36;
(b) contacting the sample with the isolated antibody of claim 1 under conditions that permit binding of the polypeptide and the antigen binding molecule; and
(c) determining the number of cells presenting the polypeptide in the sample.

25. The method of claim 24, wherein the anti-CD19 scFv is a component of a CAR.

26. The method of claim 25, wherein the cells are CAR T cells.

27. A method of determining the presence or absence of a polypeptide comprising an anti-CD19 scFv comprising the amino acid sequence of SEQ ID NO:36, wherein the method comprises:

(a) providing a sample known or suspected to comprise a polypeptide comprising an anti-CD19 scFv comprising the amino acid sequence of SEQ ID NO:36;
(b) contacting the sample with the isolated antibody of claim 1 under conditions that permit binding of the polypeptide and the antibody; and
(c) detecting the presence or absence of a polypeptide:antibody complex.

28. The method of claim 27, wherein the anti-CD19 scFv is a component of a CAR.

29. The method of claim 28, wherein the cells are CAR T cells.

\* \* \* \* \*

SEQUENCE LISTING

<160> NUMBER OF SEQ ID NOS: 45

<210> SEQ ID NO 1
<211> LENGTH: 120
<212> TYPE: PRT
<213> ORGANISM: Mus musculus

<400> SEQUENCE: 1

Gln Val Gln Leu Gln Gln Ser Gly Ala Glu Leu Val Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Asn His Gly Lys Ser Leu Glu Trp Ile
        35                  40                  45

Gly Asn Phe His Pro Tyr Asn Asp Asp Thr Arg Tyr Asn Glu Lys Phe
    50                  55                  60

Lys Asp Lys Ala Lys Leu Thr Val Glu Lys Ser Ser Ser Thr Val Tyr
65                  70                  75                  80

Leu Glu Leu Ser Arg Leu Thr Tyr Asp Asp Ser Ala Val Tyr Tyr Cys
                85                  90                  95

Thr Arg Gly Asn Asp Tyr Asp Leu Tyr Gly Met Asp Tyr Trp Gly Gln
            100                 105                 110

```
Gly Thr Ser Val Thr Val Ser Ser
        115                 120

<210> SEQ ID NO 2
<211> LENGTH: 118
<212> TYPE: PRT
<213> ORGANISM: Mus musculus

<400> SEQUENCE: 2

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Val Ile Asn Pro Gly Ser Gly Gly Ile Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Leu Asp Tyr Asp Trp Phe Ala Tyr Trp Gly Gln Gly Thr
            100                 105                 110

Leu Val Thr Val Ser Ala
        115

<210> SEQ ID NO 3
<211> LENGTH: 118
<212> TYPE: PRT
<213> ORGANISM: Mus musculus

<400> SEQUENCE: 3

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Thr Pro Gly Ser Gly Gly Ser Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Leu Asp Tyr Asp Trp Phe Ala Tyr Trp Gly Gln Gly Thr
            100                 105                 110

Leu Val Thr Val Ser Ala
        115

<210> SEQ ID NO 4
<211> LENGTH: 360
<212> TYPE: DNA
<213> ORGANISM: Mus musculus

<400> SEQUENCE: 4
caggttcagc tgcagcagtc tggggctgag ctggtgaagc ctggggcctc agtgaaggtg     60
tcctgcaagg cttttggcta caccttcact acctatccaa tagagtggat gaggcagaat    120
```

```
catggaaaga gcctagagtg gattggaaat tttcatcctt acaatgatga tactaggtac      180
aatgaaaaat tcaaggacaa ggccaaattg actgtagaaa atcctctag cacagtctac       240 ttggagctca gccgattaac atatgatgac tctgctgttt attactgtac aagggggaat      300
gattacgacc tctatggtat ggactactgg ggtcaaggaa cctcagtcac cgtctcctca      360

<210> SEQ ID NO 5
<211> LENGTH: 354
<212> TYPE: DNA
<213> ORGANISM: Mus musculus

<400> SEQUENCE: 5
caggtccagc tgcagcagtc tggagctgaa ctggtaaggc ctgggacttc agtgaaggtg       60
tcctgcaagg cttctggata cgccttcact aattatttga tagagtggat aaagcagagg      120
cctggacagg ccttgagtg gattggagtg attaatcctg aagtggtgg tattaattat        180 aatgagaagt tcaagggcaa ggcaacactg acttcagaca atcctccag cactgcctac       240 atgcagctca gcagcctgac atctgatgac tctgcggtct attttctgtgc aagatggctt     300 gattacgact ggtttgctta ctggggccaa gggactctgg tcactgtctc tgca            354

<210> SEQ ID NO 6
<211> LENGTH: 354
<212> TYPE: DNA
<213> ORGANISM: Mus musculus

<400> SEQUENCE: 6
caggtccagc tgcagcagtc tggagctgag ctggtaaggc ctgggacttc agtgaaggtg       60
tcctgcaagg cctctgggta cgccttcact aattatttga tagagtgggt aaagcagagg      120
cctggacagg cctagagtg gattggagtg attactcctg aagtggcgg ttctaactac        180 aatgagaagt tcaagggcaa ggcaacactg actgcagaca atcctccag cactgcctac       240 atgcagctca gcagcctgac atctgatgac tctgcggtct acttctgtgc aagatggctt      300
gattacgact ggtttgctta ctggggccaa gggactctgg tcactgtctc tgca             354

<210> SEQ ID NO 7
<211> LENGTH: 107
<212> TYPE: PRT
<213> ORGANISM: Mus musculus

<400> SEQUENCE: 7

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Cys Asp Asp Phe Pro Leu
                85                  90                  95

Thr Phe Gly Ala Gly Thr Lys Leu Glu Leu Lys
            100                 105

<210> SEQ ID NO 8
```

```
<211> LENGTH: 107
<212> TYPE: PRT
<213> ORGANISM: Mus musculus

<400> SEQUENCE: 8

Asp Ile Lys Met Thr Gln Phe Pro Ser Ser Met Tyr Ala Ser Val Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Cys Asp Glu Phe Pro Phe
                85                  90                  95

Thr Phe Gly Gly Gly Thr Lys Leu Glu Ile Lys
            100                 105

<210> SEQ ID NO 9
<211> LENGTH: 107
<212> TYPE: PRT
<213> ORGANISM: Mus musculus

<400> SEQUENCE: 9

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Arg Gln Cys Asp Glu Phe Pro Ser
                85                  90                  95

Thr Phe Gly Gly Gly Thr Lys Leu Glu Ile Lys
            100                 105

<210> SEQ ID NO 10
<211> LENGTH: 107
<212> TYPE: PRT
<213> ORGANISM: Mus musculus

<400> SEQUENCE: 10

Asp Ile Lys Met Thr Gln Phe Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80
```

Glu Asp Met Gly Ile Tyr Tyr Cys Leu Gln Cys Asp Asp Phe Pro Leu
            85                  90                  95

Thr Phe Gly Ala Gly Thr Lys Leu Glu Leu Lys
            100                 105

<210> SEQ ID NO 11
<211> LENGTH: 321
<212> TYPE: DNA
<213> ORGANISM: Mus musculus

<400> SEQUENCE: 11
gacatcaaga tgacccagtc tccatcttcc atgtatgcat ctctaggaga gagagtcact      60
atcacttgca aggcgagtca ggacattaat acctatttaa cctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcagcag cctggagtat     240
gaagatatgg gaatttatta ttgtctacag tgtgatgatt ttccgctcac gttcggtgct     300
gggaccaagc tggagctgaa a                                                321

<210> SEQ ID NO 12
<211> LENGTH: 321
<212> TYPE: DNA
<213> ORGANISM: Mus musculus

<400> SEQUENCE: 12
gacatcaaga tgacccagtt tccatcttcc atgtatgcat ctgtaggaga gagagtcact      60
atcacttgca aggcgagtca ggacattaat agctatttaa gctggttcca gcagaaacca     120
gggaaatctc ctaagaccct gatttatcgt gcaaacagat tggtagatgg ggtcccatca     180
aggttcagtg gcagtggatc tgggcaagat tattctctca ccatcagcag cctggagtat     240
gaagatatgg gaatttatta ttgtctacag tgtgatgagt ttccgttcac gttcggaggg     300
gggaccaagc tggaaataaa a                                                321

<210> SEQ ID NO 13
<211> LENGTH: 321
<212> TYPE: DNA
<213> ORGANISM: Mus musculus

<400> SEQUENCE: 13
gacatcaaga tgacccagtc tccatcttcc atgtatgcat ctctaggaga gagagtcact      60
atcacttgca aggcgagtca ggacattaat agctatttaa gctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcagcag cctggagtat     240
gaagatatgg gaatttatta ttgtcgacag tgtgatgagt ttccgtccac gttcggaggg     300
gggaccaagc tggaaataaa a                                                321

<210> SEQ ID NO 14
<211> LENGTH: 321
<212> TYPE: DNA
<213> ORGANISM: Mus musculus

<400> SEQUENCE: 14
gacatcaaga tgacccagtt tccatcttcc atgtatgcat ctctaggaga gagagtcact      60
atcacttgca aggcgagtca ggacattaat acctatttaa cctggttcca gcagaaacca     120
gggaaatctc ctaagaccct gatctatcgt gcaaacagat tggtagatgg ggtcccatca     180

```
aggttcagtg gcagtggatc tgggcaagat tattctctca ccatcagcag cctggagtat    240
gaagatatgg gaatttatta ttgtctacag tgtgatgatt ttccgctcac gttcggtgct    300
gggaccaagc tggagctgaa a                                              321
```

<210> SEQ ID NO 15
<211> LENGTH: 7
<212> TYPE: PRT
<213> ORGANISM: Mus musculus

<400> SEQUENCE: 15

Gly Tyr Thr Phe Thr Thr Tyr
1               5

<210> SEQ ID NO 16
<211> LENGTH: 6
<212> TYPE: PRT
<213> ORGANISM: Mus musculus

<400> SEQUENCE: 16

His Pro Tyr Asn Asp Asp
1               5

<210> SEQ ID NO 17
<211> LENGTH: 11
<212> TYPE: PRT
<213> ORGANISM: Mus musculus

<400> SEQUENCE: 17

Gly Asn Asp Tyr Asp Leu Tyr Gly Met Asp Tyr
1               5                   10

<210> SEQ ID NO 18
<211> LENGTH: 11
<212> TYPE: PRT
<213> ORGANISM: Mus musculus

<400> SEQUENCE: 18

Lys Ala Ser Gln Asp Ile Asn Thr Tyr Leu Thr
1               5                   10

<210> SEQ ID NO 19
<211> LENGTH: 7
<212> TYPE: PRT
<213> ORGANISM: Mus musculus

<400> SEQUENCE: 19

Arg Ala Asn Arg Leu Val Asp
1               5

<210> SEQ ID NO 20
<211> LENGTH: 9
<212> TYPE: PRT
<213> ORGANISM: Mus musculus

<400> SEQUENCE: 20

Leu Gln Cys Asp Asp Phe Pro Leu Thr
1               5

<210> SEQ ID NO 21
<211> LENGTH: 5
<212> TYPE: PRT
<213> ORGANISM: Mus musculus

```
<400> SEQUENCE: 21

Thr Tyr Pro Ile Glu
1               5

<210> SEQ ID NO 22
<211> LENGTH: 17
<212> TYPE: PRT
<213> ORGANISM: Mus musculus

<400> SEQUENCE: 22

Asn Phe His Pro Tyr Asn Asp Asp Thr Arg Tyr Asn Glu Lys Phe Lys
1               5                   10                  15

Asp

<210> SEQ ID NO 23
<211> LENGTH: 11
<212> TYPE: PRT
<213> ORGANISM: Mus musculus

<400> SEQUENCE: 23

Gly Asn Asp Tyr Asp Leu Tyr Gly Met Asp Tyr
1               5                   10

<210> SEQ ID NO 24
<211> LENGTH: 7
<212> TYPE: PRT
<213> ORGANISM: Mus musculus

<400> SEQUENCE: 24

Gly Tyr Ala Phe Thr Asn Tyr
1               5

<210> SEQ ID NO 25
<211> LENGTH: 6
<212> TYPE: PRT
<213> ORGANISM: Mus musculus

<400> SEQUENCE: 25

Asn Pro Gly Ser Gly Gly
1               5

<210> SEQ ID NO 26
<211> LENGTH: 9
<212> TYPE: PRT
<213> ORGANISM: Mus musculus

<400> SEQUENCE: 26

Trp Leu Asp Tyr Asp Trp Phe Ala Tyr
1               5

<210> SEQ ID NO 27
<211> LENGTH: 11
<212> TYPE: PRT
<213> ORGANISM: Mus musculus

<400> SEQUENCE: 27

Lys Ala Ser Gln Asp Ile Asn Ser Tyr Leu Ser
1               5                   10

<210> SEQ ID NO 28
<211> LENGTH: 9
<212> TYPE: PRT
<213> ORGANISM: Mus musculus
```

```
<400> SEQUENCE: 28

Leu Gln Cys Asp Glu Phe Pro Phe Thr
1               5

<210> SEQ ID NO 29
<211> LENGTH: 5
<212> TYPE: PRT
<213> ORGANISM: Mus musculus

<400> SEQUENCE: 29

Asn Tyr Leu Ile Glu
1               5

<210> SEQ ID NO 30
<211> LENGTH: 17
<212> TYPE: PRT
<213> ORGANISM: Mus musculus

<400> SEQUENCE: 30

Val Ile Asn Pro Gly Ser Gly Gly Ile Asn Tyr Asn Glu Lys Phe Lys
1               5                   10                  15

Gly

<210> SEQ ID NO 31
<211> LENGTH: 6
<212> TYPE: PRT
<213> ORGANISM: Mus musculus

<400> SEQUENCE: 31

Thr Pro Gly Ser Gly Gly
1               5

<210> SEQ ID NO 32
<211> LENGTH: 9
<212> TYPE: PRT
<213> ORGANISM: Mus musculus

<400> SEQUENCE: 32

Arg Gln Cys Asp Glu Phe Pro Ser Thr
1               5

<210> SEQ ID NO 33
<211> LENGTH: 17
<212> TYPE: PRT
<213> ORGANISM: Mus musculus

<400> SEQUENCE: 33

Val Ile Thr Pro Gly Ser Gly Gly Ser Asn Tyr Asn Glu Lys Phe Lys
1               5                   10                  15

Gly

<210> SEQ ID NO 34
<211> LENGTH: 464
<212> TYPE: PRT
<213> ORGANISM: Mus musculus

<400> SEQUENCE: 34

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Ile Lys
                20                  25                  30

Pro Gly Ala Ser Val Lys Met Ser Cys Lys Ala Ser Gly Tyr Thr Phe
```

```
            35                  40                  45
Thr Ser Tyr Val Met His Trp Val Lys Gln Lys Pro Gly Gln Gly Leu
 50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
                100                 105                 110

Tyr Tyr Cys Ala Arg Gly Thr Tyr Tyr Gly Ser Arg Val Phe Asp
                115                 120                 125

Tyr Trp Gly Gln Gly Thr Thr Leu Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
                195                 200                 205

Thr Val Pro Ser Ser Thr Trp Pro Ser Glu Thr Val Thr Cys Asn Val
210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
                260                 265                 270

Thr Pro Lys Val Thr Cys Val Val Asp Ile Ser Lys Asp Asp Pro
                275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
                340                 345                 350

Ile Ser Lys Thr Lys Gly Arg Pro Lys Ala Pro Gln Val Tyr Thr Ile
                355                 360                 365

Pro Pro Pro Lys Glu Gln Met Ala Lys Asp Lys Val Ser Leu Thr Cys
        370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
                420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
        450                 455                 460
```

<210> SEQ ID NO 35
<211> LENGTH: 239
<212> TYPE: PRT
<213> ORGANISM: Mus musculus

<400> SEQUENCE: 35

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Ile Pro
            20                  25                  30

Val Thr Pro Gly Glu Ser Val Ser Ile Ser Cys Arg Ser Ser Lys Ser
        35                  40                  45

Leu Leu Asn Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 36
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

```
Met Glu Leu Ser Ser Leu Thr Ser Glu Asp Ser Ala Val Tyr Tyr Cys
                 85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Ile Val Met Thr Gln Ala Ala
    130                 135                 140

Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Tyr Pro Phe Thr Phe Gly
225                 230                 235                 240

Ala Gly Thr Lys Leu Glu Leu Lys
                245

<210> SEQ ID NO 37
<211> LENGTH: 1392
<212> TYPE: DNA
<213> ORGANISM: Mus musculus

<400> SEQUENCE: 37
atggcgtgga tctctatcat cctcttccta gtggcaacag ctataggtgt ccactcccag    60
gttcagctgc agcagtctgg ggctgagctg gtgaagcctg gggcctcagt gaaggtgtcc   120
tgcaaggctt ttggctacac cttcactacc tatccaatag agtggatgag cagaatcat   180 ggaaagagcc tagagtggat tggaaatttt catccttaca atgatgatac taggtacaat   240
gaaaaattca aggacaaggc caaattgact gtagaaaaat cctctagcac agtctacttg   300
gagctcagcc gattaacata tgatgactct gctgtttatt actgtacaag ggggaatgat   360
tacgacctct atggtatgga ctactggggt caaggaacct cagtcaccgt ctcctcagcc   420
aaaacgacac cccatctgt ctatccactg gcccctggat ctgctgccca aactaactcc    480
atggtgaccc tgggatgcct ggtcaagggc tatttccctg agccagtgac agtgacctgg   540
aactctggat ccctgtccag cggtgtgcac accttccag ctgtcctgca gtctgacctc    600
tacactctga gcagctcagt gactgtcccc tccagcacct ggcccagcga gaccgtcacc   660
tgcaacgttg cccaccccgg cagcagcacc aaggtggaca gaaaattgt gcccagggat    720 tgtggttgta agccttgcat atgtacagtc ccagaagtat catctgtctt catcttcccc   780
ccaaagccca aggatgtgct caccattact ctgactccta aggtcacgtg tgttgtggta   840
gacatcagca aggatgatcc cgaggtccag ttcagctggt ttgtagatga tgtggaggtg   900
cacacagctc agacgcaacc ccgggaggag cagttcaaca gcactttccg ctcagtcagt   960
gaacttccca tcatgcacca ggactggctc aatggcaagg agttcaaatg cagggtcaac  1020
agtgcagctt cccctgcccc catcgagaaa accatctcca aaaccaaagg cagaccgaag  1080
gctccacagg tgtacaccat tccacctccc aaggagcaga tggccaagga taaagtcagt  1140
```

-continued

```
ctgacctgca tgataacaga cttcttccct gaagacatta ctgtggagtg gcagtggaat    1200
gggcagccag cggagaacta caagaacact cagcccatca tggacacaga tggctcttac    1260
ttcgtctaca gcaagctcaa tgtgcagaag agcaactggg aggcaggaaa tactttcacc    1320
tgctctgtgt tacatgaggg cctgcacaac caccatactg agaagagcct ctcccactct    1380
cctggtaaat ga                                                         1392
```

<210> SEQ ID NO 38
<211> LENGTH: 463
<212> TYPE: PRT
<213> ORGANISM: Mus musculus

<400> SEQUENCE: 38

| | | | | | | | | | | | | | | | |
|---|---|---|---|---|---|---|---|---|---|---|---|---|---|---|---|
| Met | Ala | Trp | Ile | Ser | Ile | Ile | Leu | Phe | Leu | Val | Ala | Thr | Ala | Ile | Gly |
| 1 | | | | 5 | | | | | 10 | | | | | 15 | |
| Val | His | Ser | Gln | Val | Gln | Leu | Gln | Gln | Ser | Gly | Ala | Glu | Leu | Val | Lys |
| | | | 20 | | | | | 25 | | | | | 30 | | |
| Pro | Gly | Ala | Ser | Val | Lys | Val | Ser | Cys | Lys | Ala | Phe | Gly | Tyr | Thr | Phe |
| | | | 35 | | | | | 40 | | | | | 45 | | |
| Thr | Thr | Tyr | Pro | Ile | Glu | Trp | Met | Arg | Gln | Asn | His | Gly | Lys | Ser | Leu |
| | 50 | | | | | 55 | | | | | 60 | | | | |
| Glu | Trp | Ile | Gly | Asn | Phe | His | Pro | Tyr | Asn | Asp | Asp | Thr | Arg | Tyr | Asn |
| 65 | | | | | 70 | | | | | 75 | | | | | 80 |
| Glu | Lys | Phe | Lys | Asp | Lys | Ala | Lys | Leu | Thr | Val | Glu | Lys | Ser | Ser | Ser |
| | | | | 85 | | | | | 90 | | | | | 95 | |
| Thr | Val | Tyr | Leu | Glu | Leu | Ser | Arg | Leu | Thr | Tyr | Asp | Asp | Ser | Ala | Val |
| | | | 100 | | | | | 105 | | | | | 110 | | |
| Tyr | Tyr | Cys | Thr | Arg | Gly | Asn | Asp | Tyr | Asp | Leu | Tyr | Gly | Met | Asp | Tyr |
| | | 115 | | | | | 120 | | | | | 125 | | | |
| Trp | Gly | Gln | Gly | Thr | Ser | Val | Thr | Val | Ser | Ser | Ala | Lys | Thr | Thr | Pro |
| | 130 | | | | | 135 | | | | | 140 | | | | |
| Pro | Ser | Val | Tyr | Pro | Leu | Ala | Pro | Gly | Ser | Ala | Ala | Gln | Thr | Asn | Ser |
| 145 | | | | | 150 | | | | | 155 | | | | | 160 |
| Met | Val | Thr | Leu | Gly | Cys | Leu | Val | Lys | Gly | Tyr | Phe | Pro | Glu | Pro | Val |
| | | | | 165 | | | | | 170 | | | | | 175 | |
| Thr | Val | Thr | Trp | Asn | Ser | Gly | Ser | Leu | Ser | Ser | Gly | Val | His | Thr | Phe |
| | | | 180 | | | | | 185 | | | | | 190 | | |
| Pro | Ala | Val | Leu | Gln | Ser | Asp | Leu | Tyr | Thr | Leu | Ser | Ser | Ser | Val | Thr |
| | | 195 | | | | | 200 | | | | | 205 | | | |
| Val | Pro | Ser | Ser | Thr | Trp | Pro | Ser | Glu | Thr | Val | Thr | Cys | Asn | Val | Ala |
| | 210 | | | | | 215 | | | | | 220 | | | | |
| His | Pro | Ala | Ser | Ser | Thr | Lys | Val | Asp | Lys | Lys | Ile | Val | Pro | Arg | Asp |
| 225 | | | | | 230 | | | | | 235 | | | | | 240 |
| Cys | Gly | Cys | Lys | Pro | Cys | Ile | Cys | Thr | Val | Pro | Glu | Val | Ser | Ser | Val |
| | | | | 245 | | | | | 250 | | | | | 255 | |
| Phe | Ile | Phe | Pro | Pro | Lys | Pro | Lys | Asp | Val | Leu | Thr | Ile | Thr | Leu | Thr |
| | | | 260 | | | | | 265 | | | | | 270 | | |
| Pro | Lys | Val | Thr | Cys | Val | Val | Val | Asp | Ile | Ser | Lys | Asp | Asp | Pro | Glu |
| | | 275 | | | | | 280 | | | | | 285 | | | |
| Val | Gln | Phe | Ser | Trp | Phe | Val | Asp | Asp | Val | Glu | Val | His | Thr | Ala | Gln |
| | 290 | | | | | 295 | | | | | 300 | | | | |
| Thr | Gln | Pro | Arg | Glu | Glu | Gln | Phe | Asn | Ser | Thr | Phe | Arg | Ser | Val | Ser |
| 305 | | | | | 310 | | | | | 315 | | | | | 320 |

```
Glu Leu Pro Ile Met His Gln Asp Trp Leu Asn Gly Lys Glu Phe Lys
            325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Asp Lys Val Ser Leu Thr Cys Met
370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
            405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
            435                 440                 445

His Asn His His Thr Glu Lys Ser Leu Ser His Ser Pro Gly Lys
            450                 455                 460

<210> SEQ ID NO 39
<211> LENGTH: 444
<212> TYPE: PRT
<213> ORGANISM: Mus musculus

<400> SEQUENCE: 39

Gln Val Gln Leu Gln Gln Ser Gly Ala Glu Leu Val Lys Pro Gly Ala
1               5                   10                  15

Ser Val Lys Val Ser Cys Lys Ala Phe Gly Tyr Thr Phe Thr Thr Tyr
            20                  25                  30

Pro Ile Glu Trp Met Arg Gln Asn His Gly Lys Ser Leu Glu Trp Ile
            35                  40                  45

Gly Asn Phe His Pro Tyr Asn Asp Asp Thr Arg Tyr Asn Glu Lys Phe
    50                  55                  60

Lys Asp Lys Ala Lys Leu Thr Val Glu Lys Ser Ser Ser Thr Val Tyr
65                  70                  75                  80

Leu Glu Leu Ser Arg Leu Thr Tyr Asp Asp Ser Ala Val Tyr Tyr Cys
                85                  90                  95

Thr Arg Gly Asn Asp Tyr Asp Leu Tyr Gly Met Asp Tyr Trp Gly Gln
            100                 105                 110

Gly Thr Ser Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
            210                 215                 220

Lys Pro Cys Ile Cys Thr Val Pro Glu Val Ser Ser Val Phe Ile Phe
225                 230                 235                 240
```

-continued

```
Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440
```

<210> SEQ ID NO 40
<211> LENGTH: 705
<212> TYPE: DNA
<213> ORGANISM: Mus musculus

<400> SEQUENCE: 40

```
atgaggaccc ctgctcagtt tcttggaatc ttgttgctct ggtttccagg tatcaaatgt    60
gacatcaaga tgacccagtc tccatcttcc atgtatgcat ctctaggaga gagagtcact   120
atcacttgca aggcgagtca ggacattaat acctatttaa cctggttcca gcagaaacca   180
gggaaatctc ctaagaccct gatctatcgt gcaaacagat tggtagatgg ggtcccatca   240
aggttcagtg gcagtggatc tgggcaagat tattctctca ccatcagcag cctggagtat   300
gaagatatgg gaatttatta ttgtctacag tgtgatgatt ttccgctcac gttcggtgct   360
gggaccaagc tggagctgaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag               705
```

<210> SEQ ID NO 41
<211> LENGTH: 234
<212> TYPE: PRT
<213> ORGANISM: Mus musculus

<400> SEQUENCE: 41

```
Met Arg Thr Pro Ala Gln Phe Leu Gly Ile Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Thr Tyr Leu Thr Trp Phe Gln Gln Lys Pro Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Gln Cys Asp
            100                 105                 110

Asp Phe Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 42
<211> LENGTH: 214
<212> TYPE: PRT
<213> ORGANISM: Mus musculus

<400> SEQUENCE: 42

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Cys Asp Asp Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
```

```
                130                 135                 140
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210
```

<210> SEQ ID NO 43
<211> LENGTH: 237
<212> TYPE: PRT
<213> ORGANISM: Mus musculus

<400> SEQUENCE: 43

```
Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
                35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
                100                 105                 110

Gln Gly Thr Thr Leu Thr Val Ser Ser Ala Lys Thr Thr Pro Pro Ser
                115                 120                 125

Val Tyr Pro Leu Ala Pro Gly Ser Ala Ala Gln Thr Asn Ser Met Val
                130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
                180                 185                 190

Ser Ser Thr Trp Pro Ser Glu Thr Val Thr Cys Asn Val Ala His Pro
                195                 200                 205

Ala Ser Ser Thr Lys Val Asp Lys Lys Ile Val Pro Arg Asp Cys Gly
                210                 215                 220

Cys Lys Pro Cys Ile Cys Thr Val Pro Glu Val Ser Ser
225                 230                 235
```

<210> SEQ ID NO 44
<211> LENGTH: 112
<212> TYPE: PRT
<213> ORGANISM: Mus musculus

<400> SEQUENCE: 44

Asp Ile Val Met Thr Gln Ala Ala Pro Ser Ile Pro Val Thr Pro Gly

```
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
                35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
                100                 105                 110

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 45

His His His His His His His His
1               5
```